US010384028B2

(12) United States Patent
Allum et al.

(10) Patent No.: US 10,384,028 B2
(45) Date of Patent: Aug. 20, 2019

(54) NASAL INTERFACE APPARATUS AND SYSTEMS FOR USE WITH A RESPIRATORY ASSIST DEVICE

(71) Applicant: SILVERBOW DEVELOPMENT LLC, San Ramon, CA (US)

(72) Inventors: Todd W. Allum, Livermore, CA (US); Gregory J. Kapust, San Ramon, CA (US)

(73) Assignee: SILVERBOW DEVELOPMENT, LLC, San Ramon, CA (US)

(*) Notice: Subject to any disclaimer, the term of this patent is extended or adjusted under 35 U.S.C. 154(b) by 956 days.

(21) Appl. No.: 14/427,986

(22) PCT Filed: Aug. 27, 2013

(86) PCT No.: PCT/US2013/056702
§ 371 (c)(1),
(2) Date: Mar. 12, 2015

(87) PCT Pub. No.: WO2014/042862
PCT Pub. Date: Mar. 20, 2014

(65) Prior Publication Data
US 2015/0250973 A1 Sep. 10, 2015

Related U.S. Application Data

(60) Provisional application No. 61/699,969, filed on Sep. 12, 2012.

(51) Int. Cl.
A61M 16/06 (2006.01)
A61M 16/20 (2006.01)
(Continued)

(52) U.S. Cl.
CPC .... *A61M 16/0666* (2013.01); *A61M 16/0003* (2014.02); *A61M 16/0063* (2014.02);
(Continued)

(58) Field of Classification Search
CPC .......... A61M 16/0666; A61M 16/0605; A61M 16/0622; A61M 16/0003; A61M 16/201;
(Continued)

(56) References Cited

U.S. PATENT DOCUMENTS 8,136,525 B2 * 3/2012 Lubke ................... A61M 16/06
128/205.25
D662,200 S 6/2012 Eghbal et al.
(Continued)

FOREIGN PATENT DOCUMENTS

CN 101405047 A 4/2009
CN 101455871 A 6/2009
(Continued)

OTHER PUBLICATIONS

International Search Report Application No. PCT/US2013/056702, dated Jan. 16, 2014, 3 pages.
(Continued)

Primary Examiner — Gregory A Anderson
Assistant Examiner — Margaret M Luarca
(74) Attorney, Agent, or Firm — Artegis Law Group, LLP

(57) ABSTRACT

An ambulatory assist ventilation (AA V) apparatus and system are disclosed for the delivery of a respiratory gas to assist the spontaneous breathing effort of a patient with a breathing disorder. The AA V system includes a compressed respiratory gas source, a respiratory assist device for controlling respiratory gas flow to the patient, a patient circuit tubing and a low profile nasal interface device, which does not have a dead space or hollow area where C02 can collect, for delivering the respiratory gas to the patient, wherein the nasal interface device is fluidly connected to the respiratory assist device via tubing for receiving the respiratory gas therefrom.

54 Claims, 21 Drawing Sheets

(51) Int. Cl.
*A61M 16/00* (2006.01)
*A61M 16/08* (2006.01)

(52) U.S. Cl.
CPC ...... *A61M 16/022* (2017.08); *A61M 16/0605* (2014.02); *A61M 16/0622* (2014.02); *A61M 16/0677* (2014.02); *A61M 16/201* (2014.02); *A61M 16/204* (2014.02); *A61M 16/0833* (2014.02); *A61M 16/0866* (2014.02); *A61M 2016/0021* (2013.01); *A61M 2016/0027* (2013.01); *A61M 2202/0208* (2013.01); *A61M 2205/3331* (2013.01); *A61M 2210/0618* (2013.01)

(58) Field of Classification Search
CPC ............ A61M 16/204; A61M 16/0677; A61M 16/0866; A61M 16/0816; A61M 16/0875; A61M 16/107; A61M 16/0672; Y10S 128/26; Y10S 128/912
USPC .................................................... 128/207.18
See application file for complete search history.

(56) References Cited

U.S. PATENT DOCUMENTS

| | | | |
|---|---|---|---|
| 9,132,250 | B2 | 9/2015 | Allum et al. |
| 9,180,270 | B2 | 11/2015 | Kapust et al. |
| 9,227,034 | B2 | 1/2016 | Kapust et al. |
| 9,675,774 | B2 | 6/2017 | Cipollone et al. |
| 9,730,830 | B2 * | 8/2017 | Foley ........................ A61F 5/56 |
| 9,962,512 | B2 | 5/2018 | Cipollone et al. |
| 10,046,133 | B2 | 8/2018 | Kapust et al. |
| 10,232,136 | B2 | 3/2019 | Kapust et al. |
| 2002/0029004 | A1 | 3/2002 | Starr et al. |
| 2005/0241644 | A1 | 11/2005 | Gunaratnam et al. |
| 2009/0044808 | A1 | 2/2009 | Guney et al. |
| 2009/0101154 | A1 | 4/2009 | Mutti et al. |
| 2010/0043801 | A1 | 2/2010 | Halling et al. |
| 2010/0252037 | A1 | 10/2010 | Wondka et al. |
| 2011/0240035 | A1 | 6/2011 | Gillies |
| 2012/0204870 | A1 | 8/2012 | Mcauley et al. |
| 2015/0314098 | A1 | 11/2015 | Allum et al. |

FOREIGN PATENT DOCUMENTS

| | | |
|---|---|---|
| WO | 2010115166 A1 | 10/2010 |
| WO | 2010115168 A1 | 10/2010 |
| WO | 2010115169 A1 | 10/2010 |
| WO | 2010115170 A1 | 10/2010 |
| WO | 2011029073 A1 | 3/2011 |
| WO | 2011029074 A1 | 3/2011 |

OTHER PUBLICATIONS

International search report for application No. PCT/US2013/056702, dated Jan. 16, 2014.

* cited by examiner

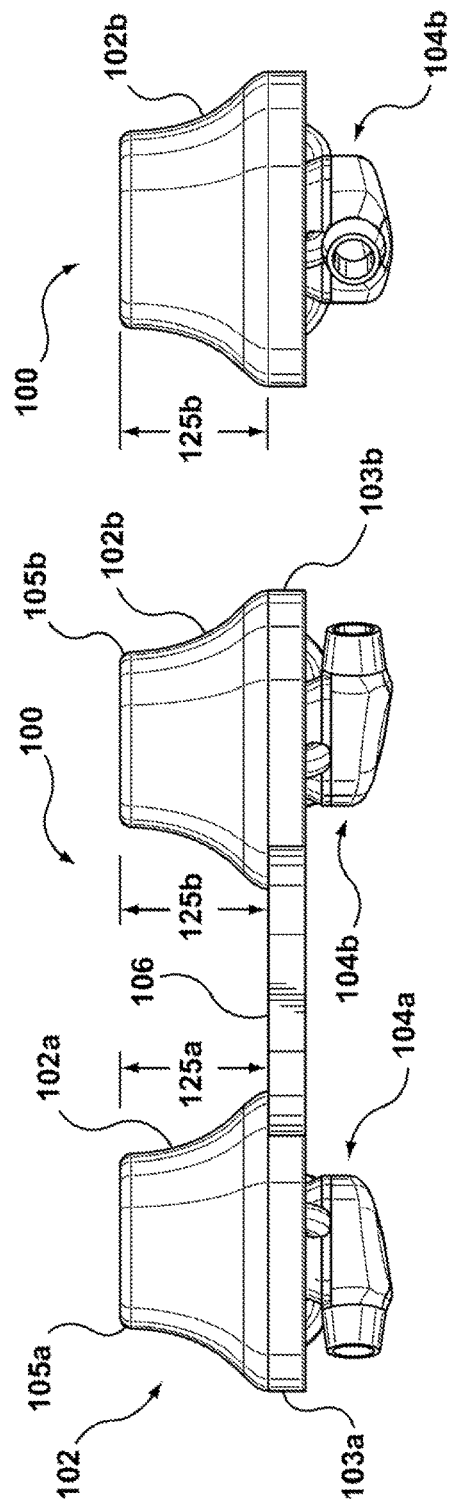
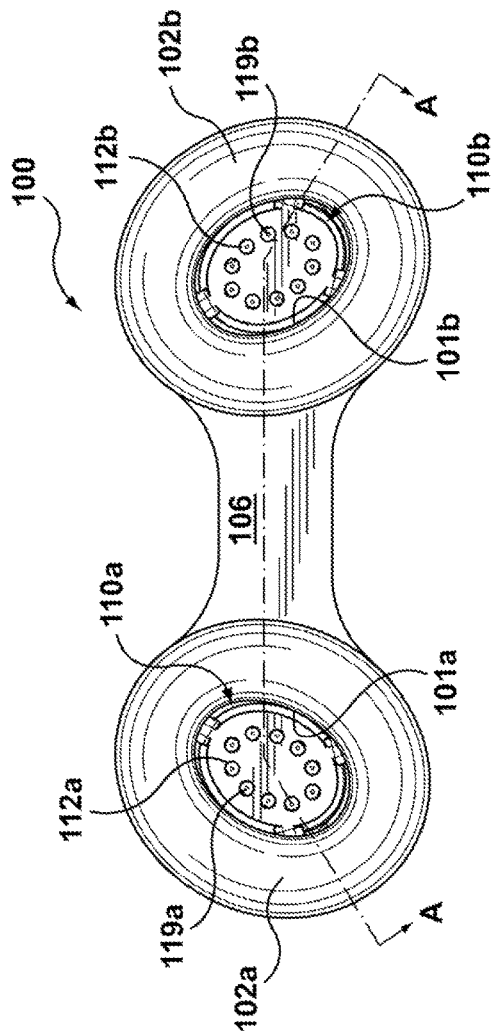

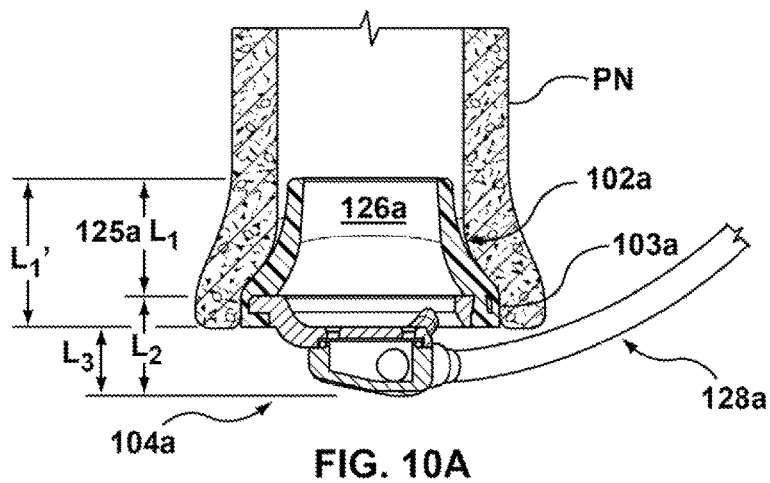
FIG. 10A
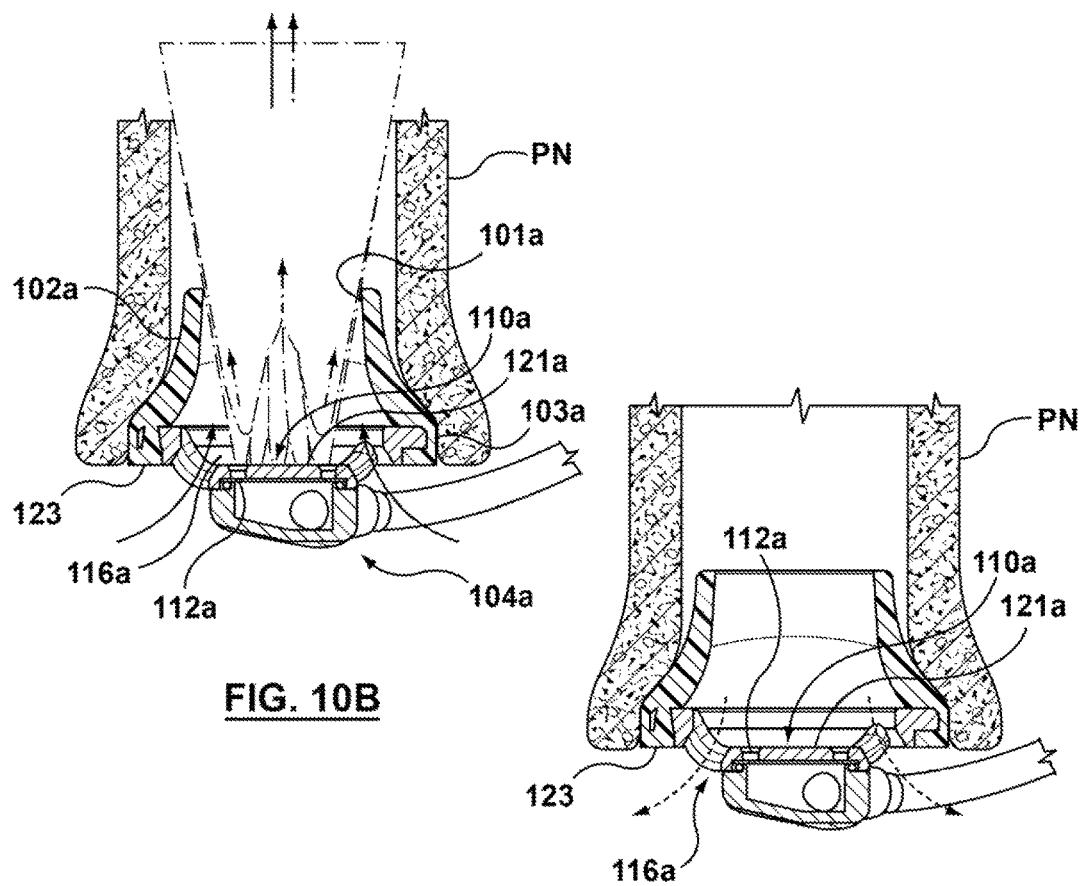
FIG. 10B
FIG. 10C

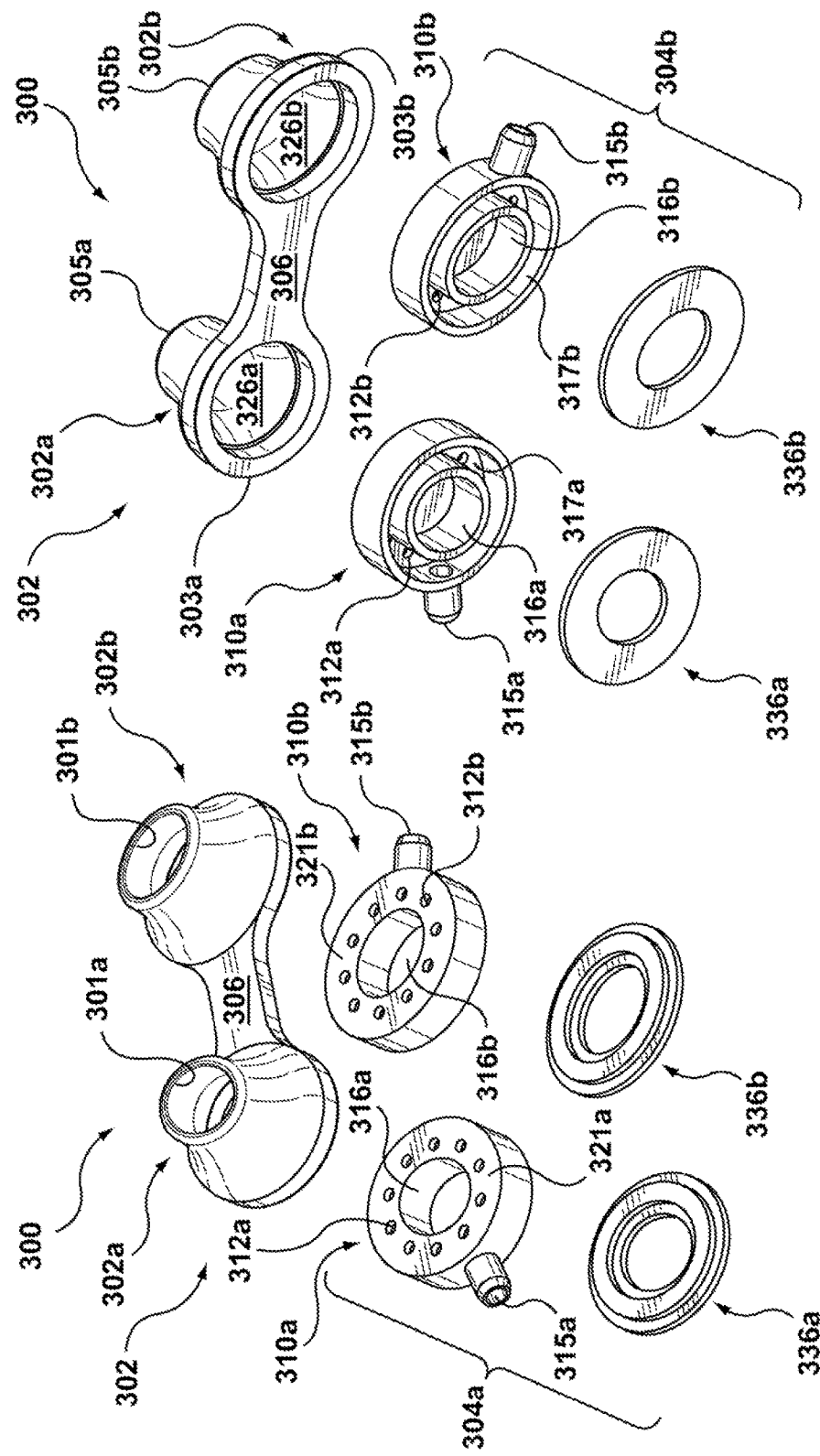

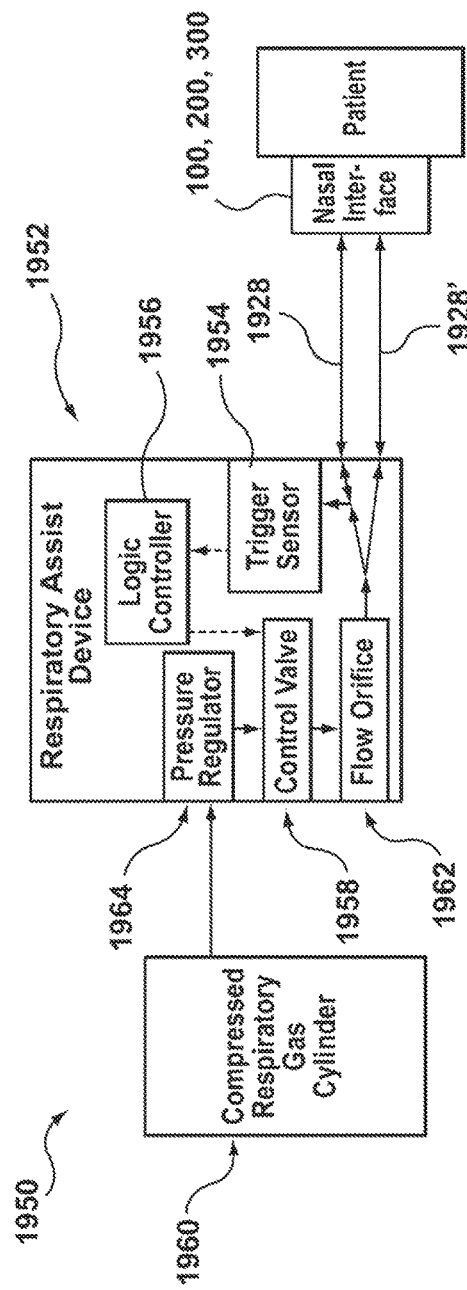
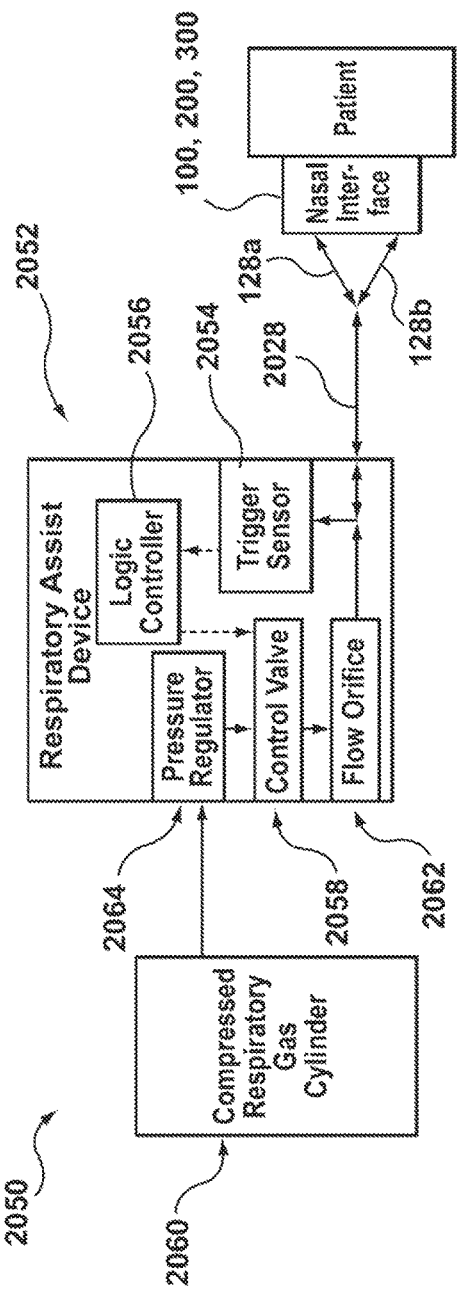
FIG. 19
FIG. 20

NASAL INTERFACE APPARATUS AND SYSTEMS FOR USE WITH A RESPIRATORY ASSIST DEVICE

CROSS-REFERENCE TO RELATED APPLICATION

This application claims the benefit of the filing date of U.S. Appl. No. 61/699,969 filed Sep. 12, 2012, the disclosure of which is incorporated by reference herein in its entirety.

FIELD OF THE INVENTION

The invention is directed to the delivery of a respiratory gas to assist the spontaneous breathing effort of a patient with a breathing disorder, and more particularly to ambulatory nasal interface apparatus and systems for delivering the respiratory gas to the patient.

BACKGROUND OF THE INVENTION

There is a need for a minimally obtrusive nasal interface, patient circuit tubing and ventilation system that delivers mechanical ventilatory support or positive airway pressure, while minimizing exhalation resistance and permitting less encumbered movement and/or ambulation of a patient so as to facilitate mobility of the patient and/or to allow activities of daily living. There are a range of clinical syndromes that require ventilation therapy that would benefit from such an interface and system, such as respiratory insufficiency, chronic obstructive lung or pulmonary disease (most commonly referred to as COPD), interstitial lung disease, fibrosis, acute respiratory distress syndrome (ARDS), airway or sleep disordered breathing, congestive heart failure and neuromuscular impairment.

There are two general types of mechanical ventilation (MV) modes. A first type delivers gas to a patient based on a frequency selected by the clinician which is independent of patient activity. This type of ventilation, known as controlled mechanical ventilation, is used when the ventilator is needed to breathe for the patient such as when the patient is non-alert, sedated, unresponsive or paralyzed. A second type of ventilation, known as assisted mechanical ventilation, or assisted ventilation, or augmented ventilation, delivers gas to the patient in response to an inspiratory effort generated by the patient. This type of ventilation helps the patient breathe, such as when the patient has respiratory insufficiency and/or dyspnea associated with COPD. There are also ventilators and modes of ventilation that combine the two modes of ventilation described above.

Certain invasive MV therapies connect to the patient by intubating the patient with a endotracheal tube, which is a tube inserted in the patient's mouth that extends to their voice box, or with a cuffed or uncuffed tracheal tube, which is a tube inserted through a stoma in the patient's throat area. While helpful in supporting the work of breathing, the patient interfaces used for invasive MV are obtrusive and/or invasive to the user, and obviously would not facilitate mobility or activities of daily living of the patient. Non-invasive mechanical ventilation (NIV) therapies also are known that ventilate a patient with a face or nasal mask rather than requiring intubation or tracheal tube. However, known non-invasive face or nasal masks are bulky and cumbersome and require a patient circuit with large diameter tubing that restricts movement and is also bulky and cumbersome. The non-invasive nasal masks used in these forms of mechanical ventilation operate using a closed gas circuit. A closed circuit system requires the mask to create a gas/air seal against the nose and/or mouth which can be uncomfortable to the patient. The bulky nature of known masks and patient circuits create a 'dead space' in the hollow areas of the mask and patient circuit. This dead space, coupled with the requirement of a closed system result in carbon dioxide ($CO_2$) accumulating in the 'dead space' or hollow areas of the mask and patient circuit. The accumulation of $CO_2$ needs to be flushed out of the patient circuit or mask to avoid the problem of the patient re-breathing $CO_2$. The $CO_2$ is flushed out the dead space by maintaining a constant low pressure in the ventilator, mask and patient circuit system. This constant low pressure creates exhalation resistance that is sometimes uncomfortable to the patient. Also, closed circuit ventilation systems increase the risk of the ventilator over pressurizing the patient's lungs, which can result in trauma to the airway tissues and then longer-term patient ventilator dependency. Consequently, known invasive and non-invasive mechanical ventilation systems do not facilitate activities of daily living of the patient or mobility and present risks of trauma to the patient's breathing tissues.

For treating sleep disorders such as sleep disordered breathing (SDB), the preferred ventilation therapies are continuous positive airway pressure (CPAP) and bi-level positive airway pressure (BiPAP). CPAP and BiPAP are a variant of mechanical non-invasive ventilation. Positive pressure applied by the ventilator in the form of CPAP or BiPAP is connected to the patient by a nasal or face mask that seals against the nose or face. The seal allows CPAP and BiPAP to operate as a closed circuit ventilation system and to treat sleep disordered breathing by pressurizing the upper airways and thereby preventing upper airway obstruction. While effective, this therapy has poor patient compliance because the patient interface and corresponding patient circuit tubing is obtrusive to the patient. As with mechanical invasive and non-invasive ventilation, the bulky nature of the CPAP and BiPAP masks and patient circuits create a 'dead space' in the hollow areas of the mask and patient circuit. This dead space, coupled with the requirement of a closed system result in $CO_2$ accumulating in the 'dead space' or hollow areas of the mask and patient circuit. The accumulation of $CO_2$ needs to be flushed out of the patient circuit or mask to avoid the problem of the patient re-breathing $CO_2$. The $CO_2$ is flushed out of the dead space by maintaining a constant low pressure in the ventilator, mask and patient circuit system. This constant low pressure creates exhalation resistance that is sometimes uncomfortable to the patient. Also, the closed circuit ventilation systems, such as CPAP and BiPAP, require the patient, in most instances, to unnaturally breathe through both a mask and gas delivery circuit, which can be uncomfortable.

Oxygen therapies are categorically different and distinct from mechanical ventilation therapies. Oxygen therapy increases the concentration of oxygen in the patient's lungs and other organs, which can increase lifespan of patients suffering from the above noted syndromes. While oxygen therapy has been demonstrated to improve lifespan, there is a lack of evidence demonstrating that oxygen therapy can reduce the severe feelings of breathlessness, work of breathing and discomfort a patient experiences resulting from the above noted syndromes. Consequently, oxygen therapies, e.g., continuous flow and pulsed flow, are used for far less severe forms of the noted syndromes than mechanical ventilation therapies. Oxygen therapies work by utilizing nasal cannulas or masks to deliver concentrated oxygen to the patient. Concentrated oxygen is delivered to the patient in a 'continuous' flow rate that is provided during the patient's inspiratory and expiratory breathing cycles, using a set continuous liter per minute (LPM) flow of oxygen. Also, concentrated oxygen is delivered to the patient in an 'intermittent' flow using oxygen therapy devices known as oxygen conservers. Oxygen conserver devices deliver an intermittent flow of oxygen only during the patient's inspiratory breathing cycle. Mechanical ventilation therapy, on the other hand, has decades of well-established evidence demonstrating a significant reduction in breathlessness, work of breathing, and discomfort experienced by patients that suffer from the above noted syndromes. Mechanical ventilation therapies can both utilize concentrated oxygen to improve lifespan and provide mechanical breathing support to improve breathing function, i.e., reduce breathlessness, work of breathing and patient discomfort. Correspondingly, mechanical ventilation therapy is different than oxygen therapy and therefore is used to treat patient populations with more severe forms of the above noted syndromes.

One or more of the above-identified disadvantages of known therapies has been attempted to be solved by a non-invasive open ventilation (NIOV) system recently developed by Breathe Technologies, Inc. of Irvine, Calif. that is used with bottled oxygen to deliver augmented $O_2$ tidal volume and entrained air during a patient's spontaneous breathing so as to deliver both ventilation and supplemental oxygen with every breath. This volume augmentation is provided via a nasal pillow interface having entrainment ports that are open to ambient air. Generally the system senses the patient's spontaneous breath through a sense port in the nasal interface, and then delivers the selected pressurized volume of oxygen. As oxygen is delivered, ambient air is entrained through the entrainment ports, and positive pressure is developed within the interface to supplement the patient's spontaneous breathing. Although the NIOV system facilitates mobility and activities of daily living, the nasal pillow interface circumferentially extends from below the patient's nose to partially circumscribe the patient's face on either side thereof in order to have a length that can accommodate a throat area of the interface, which is necessary to develop positive pressure within the interface prior to delivery of the air oxygen mixture to the patient. This throat area that circumscribes the patient's face also creates a 'dead space' in the hollow areas of the nasal pillow interface. In addition, the nasal interface requires a patient circuit with tubing that accommodates a first lumen for sensing the patient's breathing effort and a second lumen for delivering a pressurized volume of oxygen to the patient. Consequently, a diameter of tubing used with the nasal interface and patient circuit must have an overall larger outer diameter to accommodate the requirement of distinct sensing and delivery lumens. Thus when worn by the patient, the overall size and weight of the nasal interface and patient circuit tubing associated therewith is not insubstantial and may even be considered by some patients as cumbersome and/or burdensome.

Accordingly, there still exists a need in the art for minimally obtrusive nasal interfaces and patient circuits that deliver mechanical ventilatory support or positive airway pressure, while permitting less encumbered movement so as to facilitate mobility of the patient and to allow activities of daily living. Embodiments hereof are directed to a low profile and light weight nasal interface that is configured to provide improved entrainment of ambient air so as to conserve the amount of compressed respiratory gas used by a patient while providing increased ventilatory support and/or positive airway pressure.

BRIEF SUMMARY OF THE INVENTION

An ambulatory assist ventilation (AAV) apparatus and system are disclosed for the delivery of a respiratory gas to assist the spontaneous breathing effort of a patient with a breathing disorder. The AAV system includes a compressed respiratory gas source, a respiratory assist device for controlling respiratory gas flow, and a low profile open nasal interface device, which does not have a dead space or hollow area where $CO_2$ can collect, and patient circuit tubing for delivering the respiratory gas to the patient, wherein the nasal interface device is fluidly connected to the respiratory assist device via tubing for receiving the respiratory gas therefrom. The nasal interface device operates under the Venturi principle by utilizing the energy of the delivered respiratory gas to entrain ambient air and increase airway pressure thereby increasing the net volume delivered to the patient. Embodiments of nasal interface device disclosed herein are configured in an open, compact, low profile manner, which does not have a dead space or hollow area where $CO_2$ can collect, and are significantly smaller, lighter in weight and higher performing as compared to known breathing masks.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a nasal interface device in accordance with an embodiment hereof.

FIG. 2 is an end view of the nasal interface device of FIG. 1.

FIG. 3 is a top view of the nasal interface device of FIG. 1.

FIG. 10A is a sectional view of a portion of the nasal interface apparatus within a patient's nostril as shown in FIG. 10 taken along line A-A thereof.

FIG. 10B is the sectional view of the portion of the nasal interface apparatus shown in FIG. 10A depicting the delivery of a respiratory gas during an inspiratory effort of the patient.

FIG. 10C is the sectional view of the portion of the nasal interface apparatus shown in FIG. 10A depicting an expiratory effort of the patient.

FIGS. 17 and 18 are exploded perspective views of the nasal interface device of FIG. 16 showing various subcomponents thereof.

FIGS. 19 and 20 are schematic depictions of ambulatory assist ventilation (AAV) systems in accordance with embodiments hereof.

DETAILED DESCRIPTION OF THE INVENTION

Specific embodiments of the present invention are now described with reference to the figures, wherein like reference numbers indicate identical or functionally similar elements. The terms "proximal" and "distal" are used in the following description with respect to a position or direction relative to the respiratory assist device. "Proximal" and "proximally" are a position near from or in a direction toward the respiratory assist device. "Distal" or "distally" are a position distant or in a direction away from the respiratory assist device.

The following detailed description is merely exemplary in nature and is not intended to limit the invention or the application and uses of the invention. Although the descriptions of embodiments hereof are in the context of treatment of a range of clinical syndromes that require respiratory assistance, the invention may also be used in any other therapies and/or situations where it is deemed useful. Furthermore, there is no intention to be bound by any expressed or implied theory presented in the preceding technical field, background, brief summary or the following detailed description.

Figure 4:
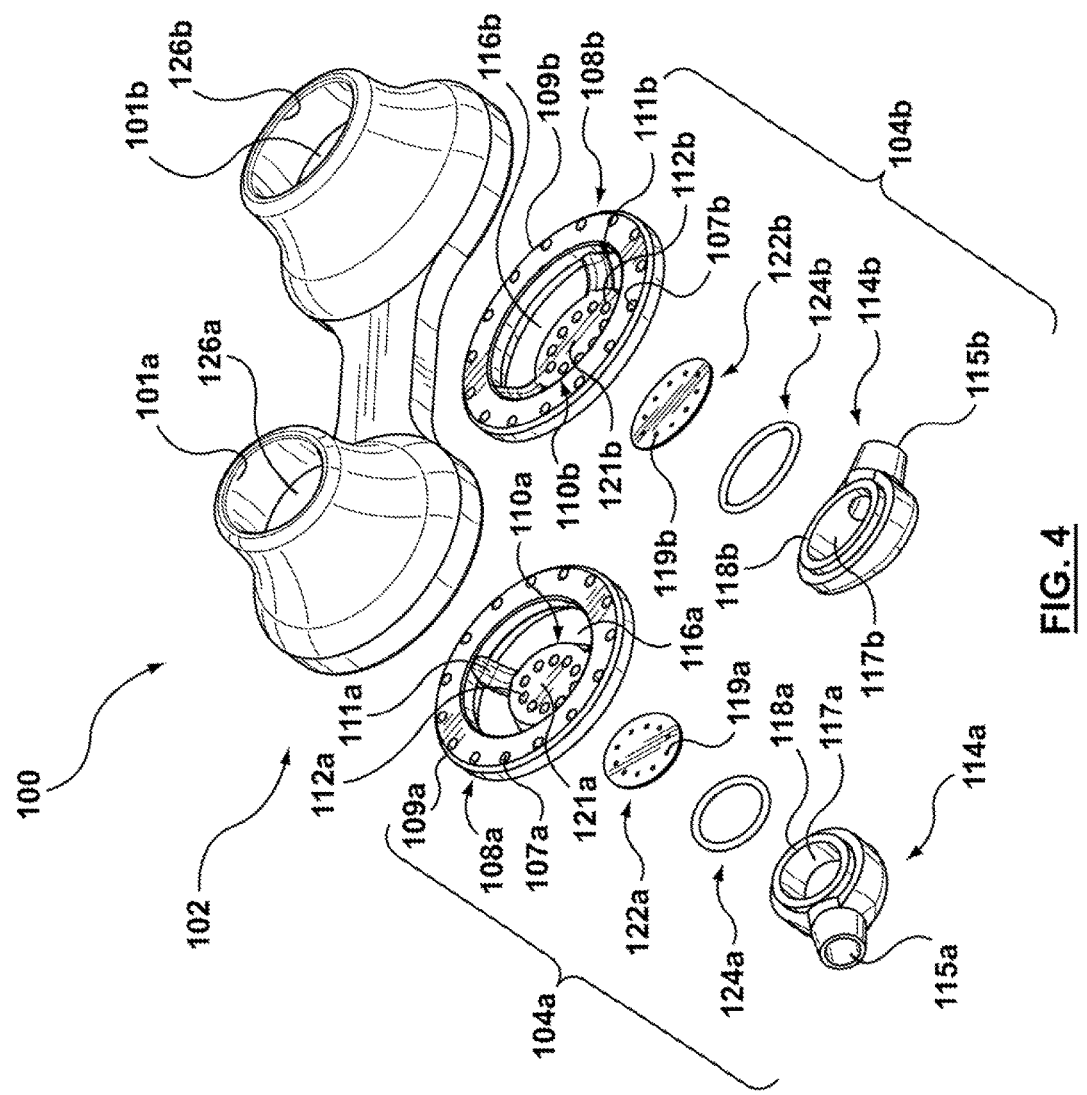
FIGS. 4 and 5 are exploded perspective views of the nasal interface device of FIG. 1 showing various subcomponents thereof.
Figure 5:
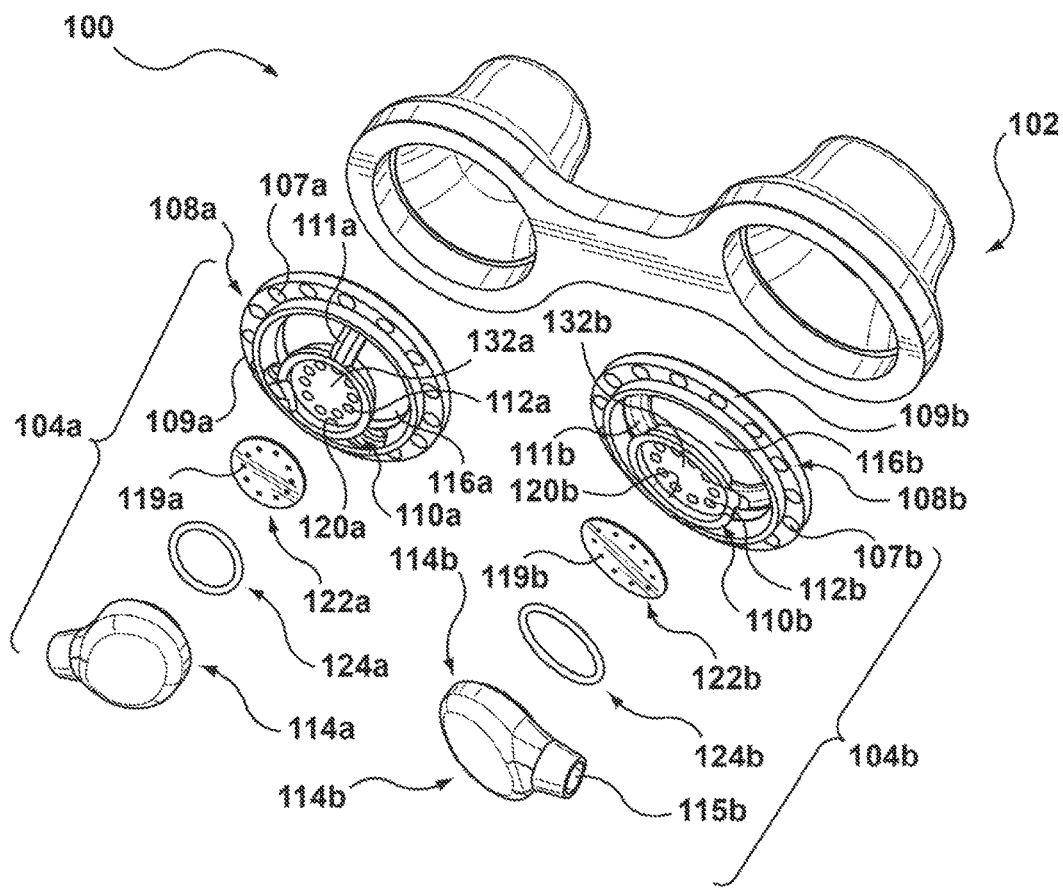
Figure 6:
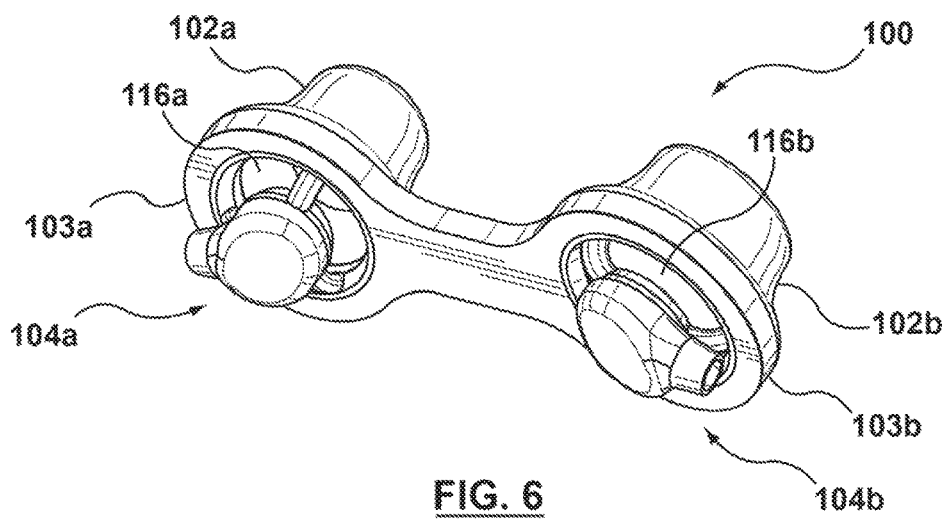
FIG. 6 is a perspective bottom view of the nasal interface device of FIG. 1.
Figure 7:
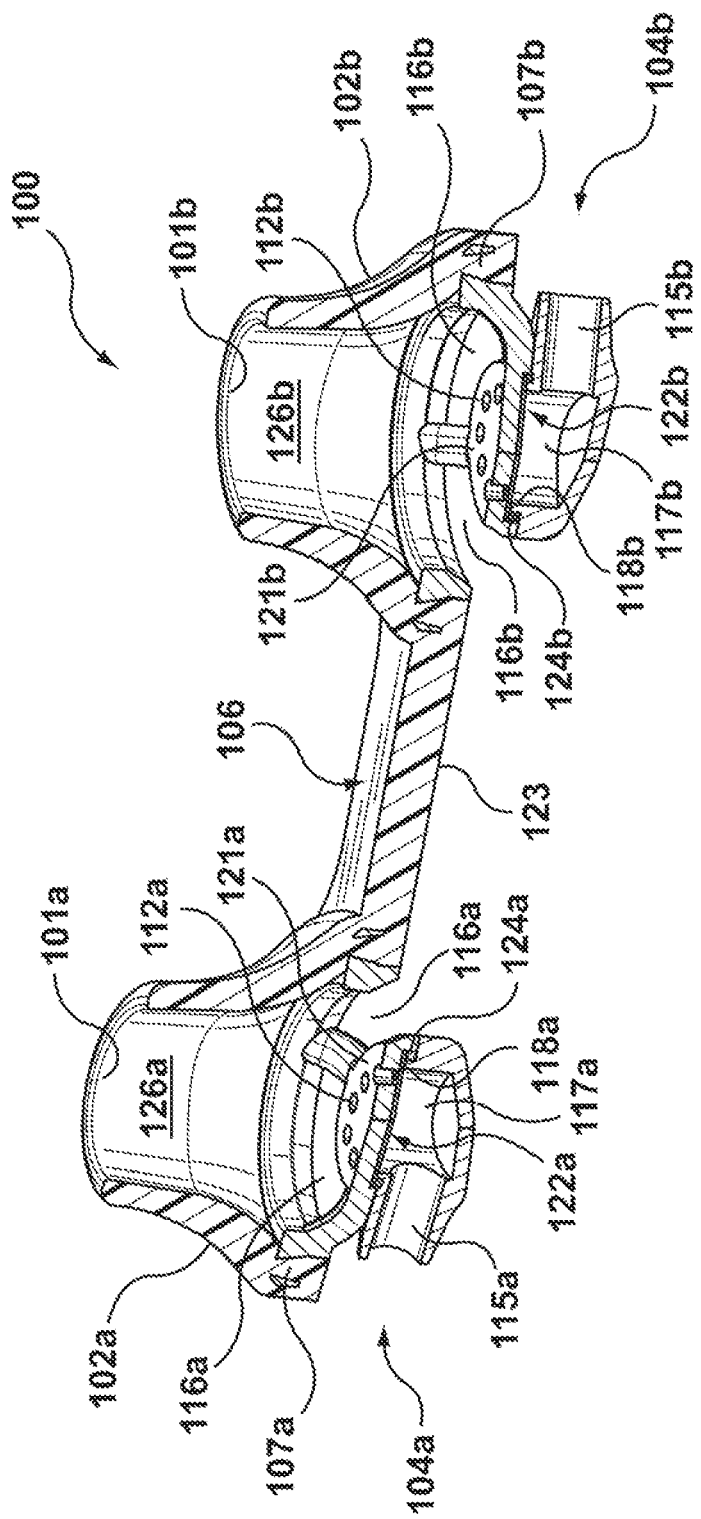
FIG. 7 is a sectional view of the nasal interface device of FIG. 3 taken along line A-A thereof.

FIGS. 1-7 depict various views of a nasal interface device 100 in accordance with an embodiment hereof. FIGS. 1, 2 and 3 are side, end and top views, respectively, of nasal interface 100 with FIGS. 4 and 5 being exploded perspective views of nasal interface 100 that show the various components thereof. FIG. 6 is a perspective bottom view of nasal interface 100, whereas FIG. 7 is a sectional view of nasal interface 100 taken along line A-A of FIG. 3.

Nasal interface 100 is used with a respiratory assist device that doses compressed respiratory gas from a compressed respiratory gas source, as will be described in more detail below. Generally, nasal interface 100 is configured to be worn by a user to deliver a mixture of respiratory gas and entrained ambient air during an inspiratory effort of the patient and to permit exhalation therethrough during an expiratory effort of the patient, which will also be described in more detail below.

Nasal interface 100 includes a nasal pillow component 102 and a pair of hub components 104a, 104b. Nasal pillow component 102 includes nasal pillows 102a, 102b that are tubular structures with proximal or first ends 103a, 103b and distal or second ends 105a, 105b. A central passageway 126a, 126b is defined by tubular body portions 125a, 125b of each nasal pillow 102a, 102b from substantially a first end 103a, 103b to a respective second end 105a, 105b thereof. In embodiments hereof, at least each of tubular body portions 125a, 125b of nasal pillows 102a, 102b is configured to have an ergonomic oval cross-section along an entire length thereof and are intended to be inserted in their entirety into the nasal cavity to assist in anchoring nasal interface 100 within a user's nostrils. A connector strip 106 is a thin flexible segment of nasal pillow component 102 that extends between first ends 103a, 103b of nasal pillows 102a, 102b, respectively, to provide flexibility and articulation between nasal pillows 102a, 102b so as to permit adjustment to the particular anatomy of a user. In embodiments hereof, connector strip 106 may be a sinusoidal strip, two or more, parallel strips, or a chain or series of oval or circular shapes that extend between nasal pillows 102a, 102b, respectively. In an embodiment, nasal pillow component 102 with nasal pillows 102a, 102b and connector strip 106 is a molded component of an elastomeric material, such as 30 Shore A silicone. The pillows do not require or include a "bulge" or shock absorber section that are typically found in the art to permit the pillows to articulate and compress to fit and seal against the anatomy of a user because the connector strip 106, allows the nasal pillow components to independently articulate in order for them to fit entirely into the user's nostrils creating an airtight seal.

Hub components 104a, 104b are concentrically disposed with first ends 103a, 103b of nasal pillows 102a, 102b, respectively. With reference to the exploded views of nasal interface 100 depicted in FIGS. 4 and 5, each hub component 104a, 104b includes a distal support structure 108a, 108b, a central hub 110a, 110b with a plurality of delivery openings 112a, 112b, and a proximal plenum structure 114a, 114b. The plurality of delivery openings 112a, 112b of each hub component 104a, 104b are periodically spaced about a perimeter of a distal face 121a, 121b of respective central hub 110a, 110b. In an embodiment, each delivery opening 112a, 112b has a substantially circular cross-section. Proximal plenum structures 114a, 114b in conjunction with central hub 110a, 110b form an enclosed space or plenum in which the air pressure is elevated above ambient pressure. Distal support structures 108a, 108b include annular rims 109a, 109b and spokes or struts 111a, 111b that radially extend between annular rims 109a, 109b and respective central hubs 110a, 110b. Although shown with three spokes 111a, 111b, more or fewer spokes may be used in support structures 108a, 108b in accordance with various embodiments hereof. In an embodiment, each support structure 108a, 108b and its respective central hub 110a, 110b is a single molded component of a polycarbonate. A series of ambient air apertures 116a, 116b are formed between respective annular rims 109a, 109b, adjacent spokes 111a, 111b and central hubs 110a, 110b, such that as shown in FIGS. 6 and 7, the series of ambient air apertures 116a, 116b of nasal interface 100 are disposed proximate first ends 103a, 103b of each nasal pillow 102a, 102b, respectively, to substantially surround the respective central hub 110a, 110b disposed therein.

Central hubs 110a, 110b of hub components 104a, 104b are positioned to be coaxial with respective distal ports 101a, 101b of nasal pillows 102a, 102b such that the plurality of delivery openings 112a, 112b of each hub are positioned to deliver a respiratory gas within its respective nasal pillow. Proximal plenum structures 114a, 114b of hub components 104a, 104b define an inlet 115a, 115b for receiving a respiratory gas from the respiratory assist device (not shown) and a plenum or chamber 117a, 117b for distributing the respiratory gas to the plurality of delivery openings 112a, 112b of respective central hubs 110a, 110b. Proximal plenum structures 114a, 114b include distally extending annular flanges 118a, 118b that snap, or are otherwise secured by ultrasonically welding or gluing, within corresponding proximal recesses 120a, 120b within central hubs 110a, 110b. In an embodiment, plenum structures 114a, 114b are molded components of a polycarbonate or acrylonitrile butadiene styrene (ABS).

Hub components 104a, 104b further include outlet discs 122a, 122b having a plurality of outlets or holes 119a, 119b and seals 124a, 124b. In an embodiment, outlet discs 122a, 122b are formed from a thin sheet of a metal, such as stainless steel or brass, with outlets 119a, 119b formed therethrough by electrochemical etching. In an embodiment, outlet discs 122a, 122b have a thickness or depth of less than 0.040 inch with each outlet 119a, 119b having a diameter of less than 0.010 inch. In another embodiment, outlet discs 122a, 122b have a thickness or depth that is less than a diameter of each outlet 119a, 119b, e.g., an outlet disc thickness or depth of 0.005 inch and an outlet diameter of 0.010 inch. The plurality of outlets 119a, 119b of outlet discs 122a, 122b correspond in number and orientation to the plurality of delivery openings 112a, 112b of respective central hubs 110a, 110b. In an embodiment, each of the delivery openings 112a, 112b has a diameter that is slightly greater than the diameter of a corresponding disc outlet with each delivery opening 112a, 112b being sized to be large enough to not impede on the flow exiting from a corresponding disc outlet 119a, 119b. Outlet discs 122a, 122b and seals 124a, 124b are disposed within proximal recesses 120a, 120b of central hubs 110a, 110b such that disc outlets 119a, 119b substantially align with corresponding central hub delivery openings 112a, 112b. The configuration of each disc outlet 119a, 119b, i.e., diameter and depth, and respective larger hub delivery opening 112a, 112b provides for a softer more diffusive gas flow to the patient such that the patient is less likely to experience discomfort due to flow impingement, most particularly if the disc outlet thickness or depth is less than a diameter of the disc outlet. In the embodiment of FIGS. 1-7, outlet discs 122a, 122b and central hubs 110a, 110b are oval. In order to assure alignment of disc outlets 119a, 119b and delivery openings 112a, 112b, outlet discs 122a, 122b are held or pressed against respective proximal faces 132a, 132b of central hubs 110a, 110b by respective annular flanges 118a, 118b of proximal plenum structures 114a, 114b with seals 124a, 124b therebetween.

Hub components 104a, 104b, as described above, are attached to nasal pillow component 102 by respective annular rims 109a, 109b, each of which in the embodiment shown in FIGS. 4 and 5 includes a series of post-forming apertures 107a, 107b that receive a material of nasal pillow component 102 there through in an over-molding process that is used to connect the structures together, as best seen in the sectional view of nasal interface 100 shown in FIG. 7. In another embodiment, nasal pillow component 102 may be glued or otherwise attached to annular rims 109a, 109b of hub components 104a, 104b.

As shown in FIG. 3, a pattern of the plurality of disc outlets 119a, 119b and delivery openings 112a, 112b of central hubs 110a, 110b, respectively, are shaped and positioned to correspond with the respective distal port 101a, 101b of nasal pillows 102a, 102b so that the flow of a respiratory gas from the plurality of disc outlets 119a, 119b and delivery openings 112a, 112b in conjunction with ambient air that is entrained by the respiratory gas flow from ambient air apertures 116a, 116b substantially fills the respective proximal port 101a, 101b prior to entering a respective nare of the patient, which will be explained in more detail below with reference to FIGS. 10A through 10C. In the embodiment of FIG. 3, the plurality of disc outlets 119a, 119b and delivery openings 112a, 112b are in a pattern that corresponds to a shape of the respective proximal port 101a, 101b of nasal pillows 102a, 102b. In various other embodiments, the plurality of disc outlets 119a, 119b and delivery openings 112a, 112b may be arranged to form, for example, a circular, polygonal or cross pattern or a series of parallel lines through a respective central hub 110a, 110b that is configured such that the respective nasal pillow proximal port 101a, 101b is filled with the respiratory gas/ambient air outflow stream that is created thereby. In various embodiments hereof, an outlet disc may be omitted with the plurality of delivery openings of the central hubs being sized and configured to produce/deliver the pressurized respiratory gas/entrained air outflow stream to the respective nasal pillow proximal ports.

Figure 8:
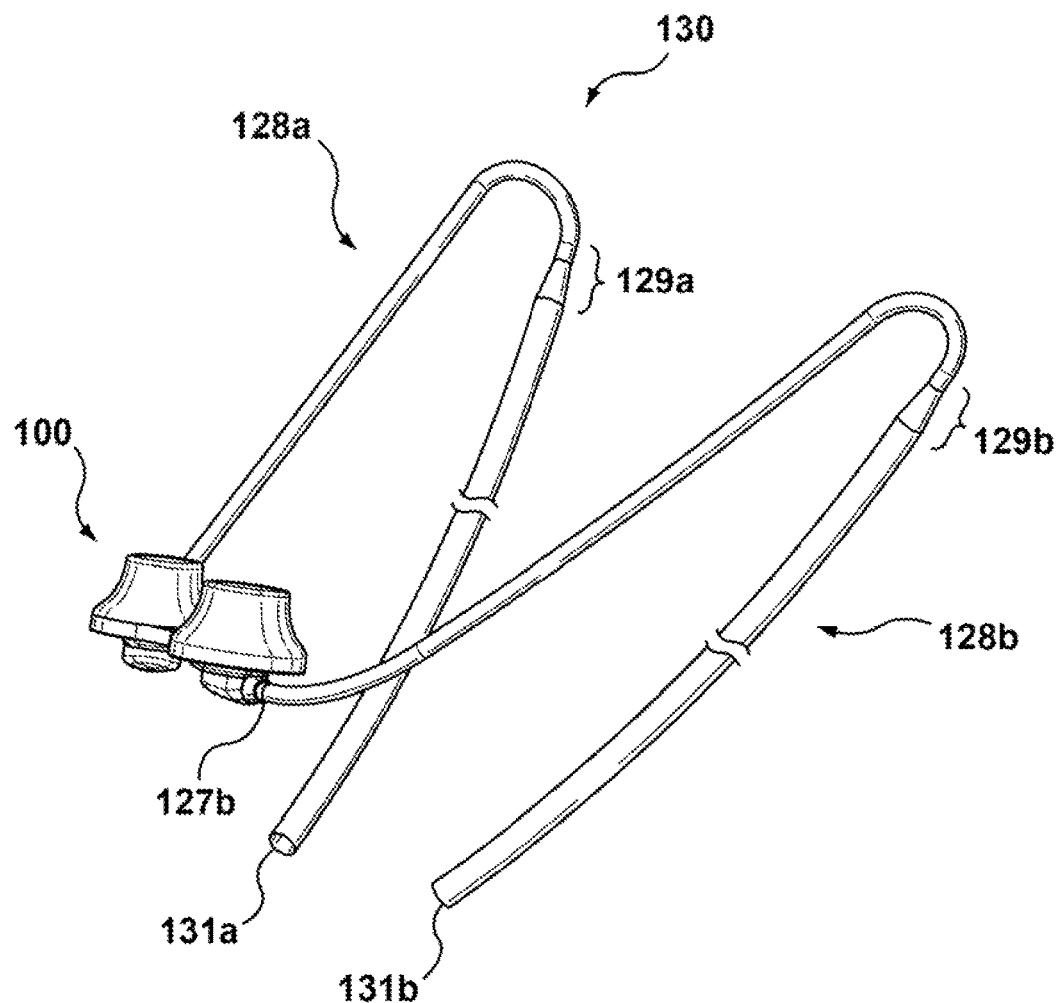
FIG. 8 is a perspective view of a nasal interface apparatus that depicts the nasal interface device of FIG. 1 connected to tubing for fluidly coupling to a respiratory assist device (not shown) and a pressurized respiratory gas source (not shown).
Figure 9:
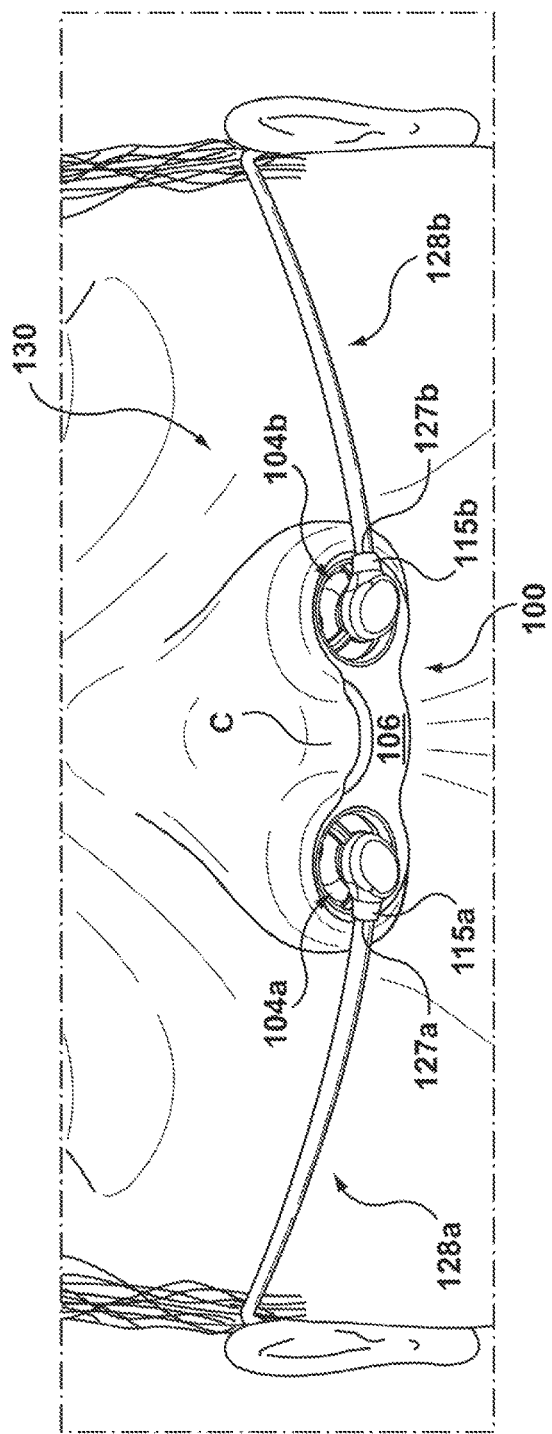
FIG. 9 is a frontal view depiction of the nasal interface apparatus as shown in FIG. 8 being worn by a patient.
Figure 10:
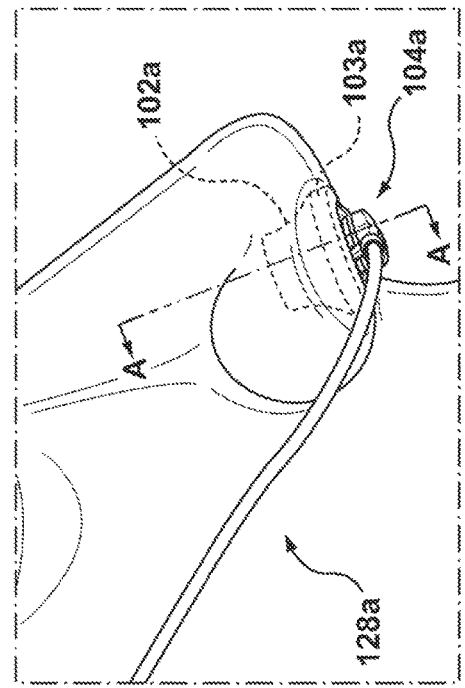
FIG. 10 is a side view depiction of the nasal interface apparatus as shown in FIG. 8 being worn by a patient.

FIG. 8 is a perspective view of a nasal interface apparatus 130 that includes nasal interface 100 connected to tubing or tubes 128a, 128b for fluidly coupling the nasal interface to a respiratory assist device (not shown) and a pressurized respiratory gas source (not shown), with FIGS. 9 and 10 being frontal and side views, respectively, depicting nasal interface apparatus 130 being worn by a patient. The unencumbering, low profile of nasal interface 100 is clearly depicted in FIGS. 9 and 10 and the minimal diameter and substantially 90° approach of tubing 128a, 128b into inlets 115a, 115b of hub components 104a, 104b adds to the overall unencumbering nature of nasal interface apparatus 130, which may help to reduce the self-consciousness of a wearer, to reduce impediment while eating and drinking, and/or to reduce interference with eye wear and facial hair, such as mustaches. Tubing 128a, 128b includes a first inner diameter from first or distal ends 127a, 127b, where each of tubing 128a, 128b connects with the respective hub component inlet 115a, 115b, to flared or stepped-up segments 129a, 129b of tubing 128a, 128b that are disposed along a length of the respective tubing that is intended to sit behind or under a patient's ear. Tubing 128a, 128b includes a second inner diameter that is greater than the first inner diameter from flared or stepped-up segments 129a, 129b to second or proximal ends 131a, 131b.

In embodiments hereof, a first inner diameter of tubing 128a, 128b may be in the range of 0.020 inch to 0.070 inch and a second inner diameter of tubing 128a, 128b may be in the range of 0.080 inch to 0.125 inch. Advantageously, the smaller first inner diameter tubing increases in diameter at flared or stepped-up segments 129a, 129b behind the patient's ear and thereby minimizes pressure drop compared to having the smaller first inner diameter tubing extend to the respiratory assist device or a Y- or T-connector. Second ends 131a, 131b of tubing 128a, 128b may each directly connect to the respiratory assist device, as depicted in the system of FIG. 19, or may connect via a T- or Y-connector to another length of tubing or hose that connects with the respiratory assist device, as depicted in the system of FIG. 20. In an embodiment, each tubing 128a, 128b may be formed from more than one segment of tubing or tubes with at least a first or proximal segment of tubing having the first inner diameter and a second or distal segment of tubing having the second inner diameter with flared or stepped-up segment 129a, 129b being a flared connector, fitting or additional segment of tubing that fluidly couples the first and second segments of tubing together while providing a gradual transition between the first and second inner diameters thereof. In another embodiment, tubing 128a, 128b may have more than one flared or stepped-up segment between the first and second ends thereof.

FIG. 10A is a simplified sectional view taken along line A-A in FIG. 10 of a patient's nostril PN with a portion of nasal interface 100 disposed therein. As depicted in FIG. 10A, a length $L_1$ of tubular body portion 125a of nasal pillow 102a is greater than a length $L_2$ of hub component 104a, with the length $L_1$ of the nasal pillow body portion being sized to fit within the nostril of a user and with a length $L_3$ being a length of hub component 104a that extends slightly proximal of the nostril opening. In embodiments hereof, a length $L_1$ of tubular body portion 125a may be in the range of 0.10 inch to 0.60 inch, a length $L_2$ of hub component 104a may be in the range of 0.05 inch to 0.40 inch and a length $L_3$ being a length of hub component 104a that extends slightly proximal of the nostril opening may be in the range of 0.050 inch to 0.30 inch. In an embodiment, a width of nasal pillow 102a at the half line, L1'/2 is equivalent to a width of the nostril opening and/or a width of hub component 104a is selected to be no wider than a rim of the nostril opening. In an embodiment, a length $L_1$ of tubular body portion 125a of nasal pillow 102a is sized to reside within the nostril of a user such that when nasal interface 100 is worn by the user connector strip 106 abuts against the columella C between the patient's nostrils while the remainder of the nasal interface 100, which includes length $L_3$ of hub component 104a, is disposed within or slightly proximal of the nostril of the user, as depicted in FIGS. 9, 10 and 10A. The use of the phrase "disposed . . . slightly proximal of the nostril of the user" is meant to convey that no part of the nasal pillow or hub component extends a distance proximal of the rim of the nostril opening that is sufficient to touch or interact with any tissue proximate or proximal of the rim of the nostril opening. In another embodiment, an overall length $L_1'$ of nasal pillow 102a is sized such that when nasal interface 100 is worn by a user the nasal pillow first end 103a does not substantially extend beyond the nostril opening of the user. In embodiments hereof, an overall length $L_1'$ of nasal pillows 102a, 102b may be in the range of 0.10 inch to 0.60 inch. The use of the phrase "does not substantially extend beyond the nostril opening of a user" is meant to convey that none of to less than a quarter of a length of the nasal pillow extends below or proximal of the rim of the nostril opening.

FIGS. 10B and 10C are sectional views taken along line A-A in FIG. 10 of a portion of nasal interface 100, with FIG. 10B depicting the delivery of respiratory gas and entrained ambient air during an inspiratory effort of the patient and FIG. 10C depicting an expiratory effort of the patient. Central hub 110a of hub component 104a is positioned at first or proximal end 103a of nasal pillow 102a so as to be substantially coaxial with distal port 101a of the nasal pillow. During an inspiratory phase of a patient wearing nasal interface apparatus 130, the flow of a pressurized respiratory gas from the plurality of delivery openings 112a of central hub 110a (represented by arrows made with dot-dashed lines in FIG. 10B) in conjunction with entrained ambient air pulled-in from ambient air apertures 116a (represented by arrows made with solid lines in FIG. 10B) produces an outflow stream that substantially fills proximal port 101a prior to exiting nasal pillow 102a and entering a respective nare of the patient. During an expiratory phase of a patient wearing nasal interface apparatus 130, the flow of the pressurized respiratory gas and thus entrainment of ambient air ceases and the patient is permitted to freely exhale through nasal interface 100 with the expired gas from the patient exiting through ambient air apertures 116a, as represented by arrows made with dashed lines in FIG. 10C. In an embodiment hereof, the size of ambient air apertures 116a, 116b and their position within nasal interface 100 to be substantially aligned with rims of the patient's nostril provides less resistance to the patient's inhalation and exhalation and particularly minimizes exhalation resistance, such that the nasal interface does not interfere with the patient's breathing out to thereby prevent undesirable "breath stacking."

In embodiments hereof, the arrangement and number of disc outlets 119a, 119b or delivery openings 112a of central hub 110a and their location proximate to or near the ambient air apertures 116a provides 300% to 400% of ambient air entrainment, which conserves the respiratory gas supply while providing a therapeutic volume of the entrained ambient air and respiratory gas mixture to the patient. In other embodiments, the arrangement and number of disc outlets 119a, 119b or delivery openings 112a of central hub 110a and their location within the nasal interface proximate to or near the ambient air apertures 116a provides a therapeutic volume of an entrained ambient air and respiratory gas mixture to the patient that has 3 to 5 times more entrained ambient air than respiratory gas, which also serves to conserve the respiratory gas supply. The afore-mentioned improvement in entrainment is realized due to the arrangement of disc outlets or delivery openings, the number of pressurized respiratory gas disc outlets or delivery openings, the minimal diameters of each disc outlet or delivery opening and the spacing, nearness and/or proximity of the disc outlet or delivery openings to the ambient air aperture(s). The arrangement of delivery openings is preferably configured in a pattern that will maximize the amount of respiratory gas flow from each of the delivery openings that is exposed to entrained ambient air while also maximizing a size of the ambient air aperture so as to permit a maximum amount of entrained ambient air to flow through and into the nasal pillows of the nasal interface. Furthermore, it is preferable to maximize the number of delivery openings, while maintaining a constant net sum of the cross-sectional areas of the openings, i.e., minimal diameters, which further increases the perimetrical amount of respiratory gas flow from each of the delivery openings that is exposed to the entrained ambient air while minimizing an internal area of the respiratory gas flow that is not exposed to the entrained ambient air. Additionally, it is preferred to locate the delivery openings in close proximity to the ambient air aperture(s) to maximize exposure of the respiratory gas flow from each delivery opening with the entrained ambient air.

The number of pressurized respiratory gas disc outlets or delivery openings, the minimal diameters of each disc outlet or delivery opening and the spacing, nearness and/or proximity of the disc outlets or delivery openings to the ambient air aperture(s) also permits the delivery of the pressurized respiratory gas relatively close to or near the entrance to the nare opening without creating discomfort to the patient due to flow impingement, and it is consideration of these factors that has led to the development of the small, lightweight and discrete nasal interfaces of embodiments hereof. The amount of fluid power exiting each discrete disc outlet or delivery opening is proportional to the mass flow rate and the square of the velocity. By design to increase entrainment and patient pressure, the fluid velocity out of each outlet or opening is sonic. Sonic flow is a physical limitation of the fluid speed exiting an outlet or opening. By minimizing the diameter of each disc outlet/delivery opening and increasing the number of disc outlets/delivery openings, the mass flow rate exiting each disc outlet/delivery opening is reduced by the total amount of outlets/openings, assuming a constant net sum of the cross-sectional areas of the openings. Therefore, for e.g., when ten outlets are to be employed as opposed to one outlet, the fluid power out of each opening would be $\frac{1}{10}$ that of a single outlet. This will reduce the discomfort transmitted to the patient do to flow impingement. With reference to FIGS. 7, 10B and 10C and as previously described above, distal surfaces 121a, 121b of central hubs 110a, 110b of hub components 104a, 104b include the plurality of delivery openings 112a, 112b formed therein with outlet discs 122a, 122b secured therein. In accordance with various nasal interface embodiments hereof, in order to affect entrainment and to assure comfortable flow to the patient, distal surfaces 121a, 121b of each central hub 110a, 110b may be one of aligned with, proximal to and distal of a proximal surface 123 of nasal pillow component 102.

Figure 11:
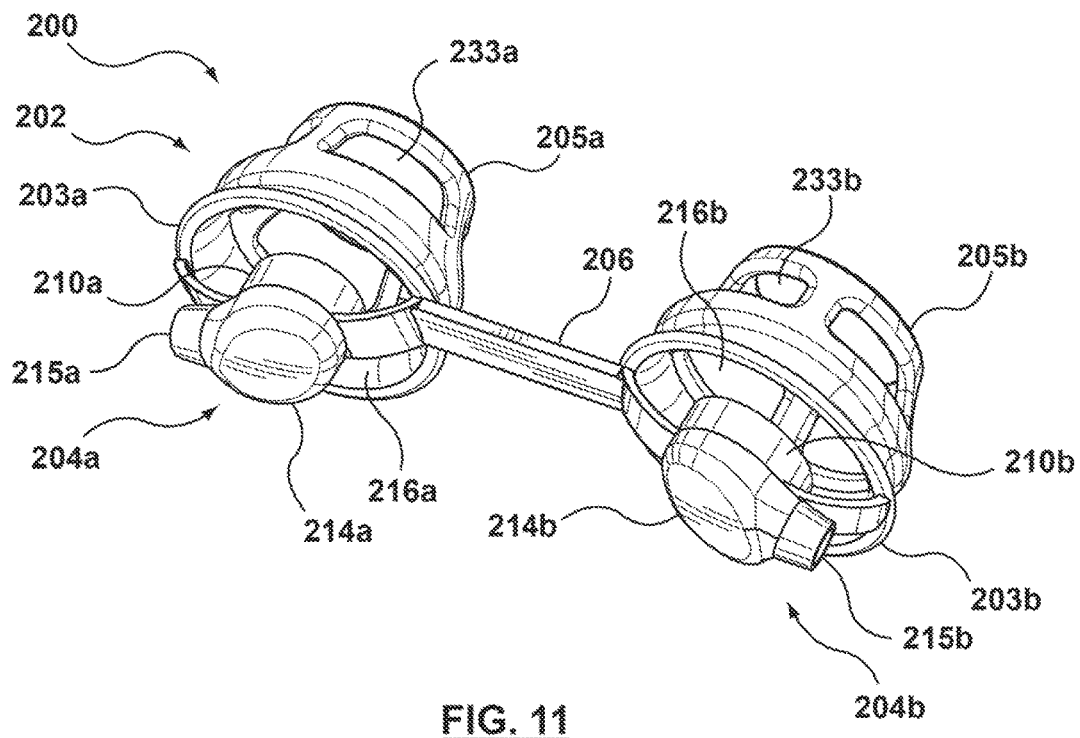
FIG. 11 is a perspective bottom view of a nasal interface device in accordance with another embodiment hereof.
Figure 12:
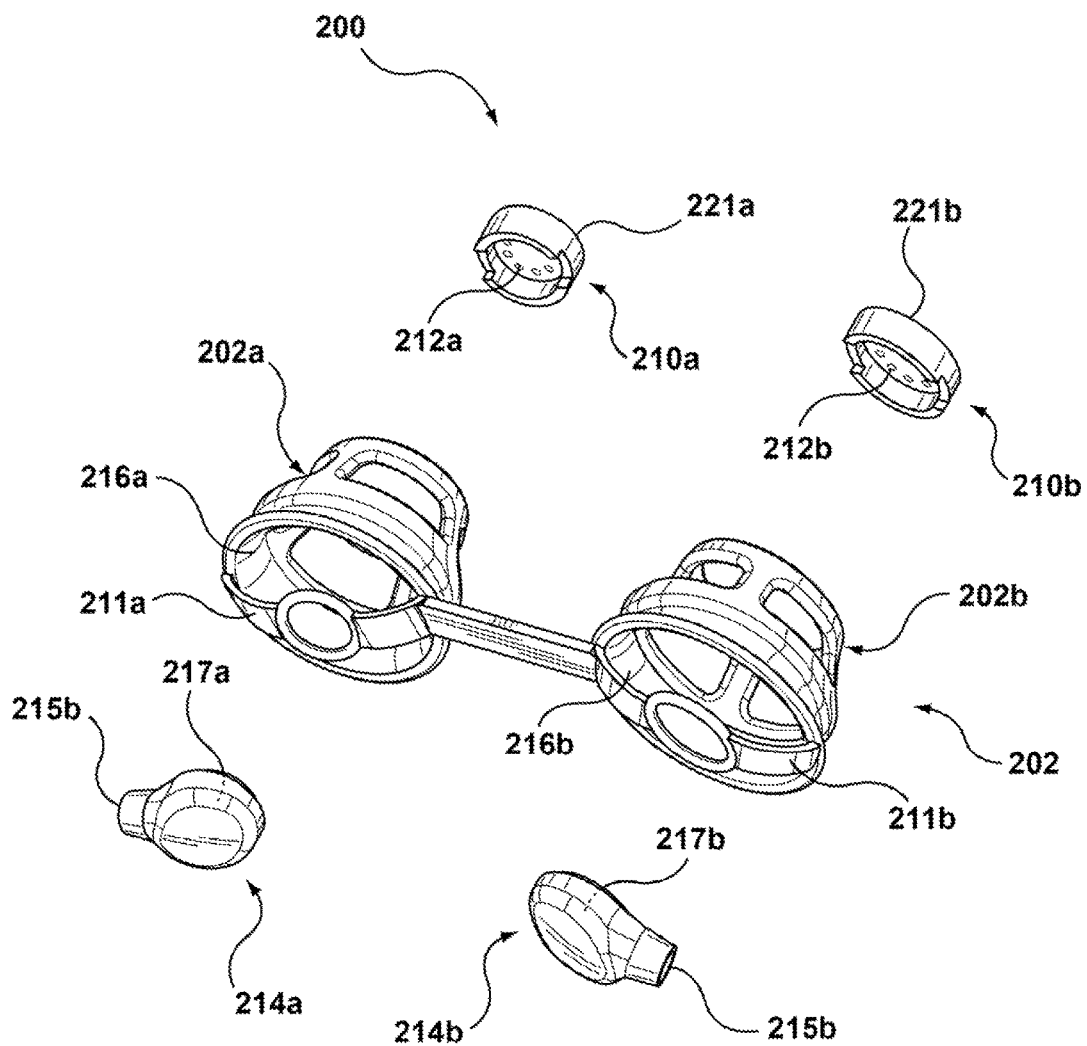
FIG. 12 is an exploded perspective view of the nasal interface device of FIG. 11 showing various subcomponents thereof.

FIG. 11 is a perspective bottom view of a nasal interface device 200 in accordance with another embodiment hereof, with FIG. 12 being an exploded perspective view of nasal interface device 200 showing various subcomponents thereof. The embodiment of FIGS. 11-15 may be used with all features described with reference to other embodiments hereof and only features and functions that differ from those already described will be detailed herein. Nasal interface 200 includes a nasal pillow component 202 and a pair of hub components 204a, 204b. Nasal pillow component 202 includes nasal pillows 202a, 202b with tubular body portions 225a, 225b having lattice-like walls that include a series of circumferentially extending apertures 233a, 233b therethrough. The lattice-like structure of nasal pillows 202a, 202b aids in anchoring the nasal pillow within a respective nare of the nasal interface wearer, while improving comfort of the wearer. Nasal pillows 202a, 202b have proximal or first ends 203a, 203b and distal or second ends 205a, 205b. A central passageway 226a, 226b is defined by tubular body portions 225a, 225b of each nasal pillow 202a, 202b from substantially a first end 203a, 203b to a respective second end 205a, 205b thereof. Nasal pillow component 202 also includes distal support structures 208a, 208b for attaching nasal pillow component 202 to hub components 204a, 204b, as described below. A connector strip 206 is a thin flexible segment of nasal pillow component 202 that extends between struts 211a, 211b proximal of first ends 203a, 203b of nasal pillows 202a, 202b, respectively, to provide flexibility and articulation between nasal pillows 202a, 202b so as to permit adjustment to the particular anatomy of a user.

Figure 13:
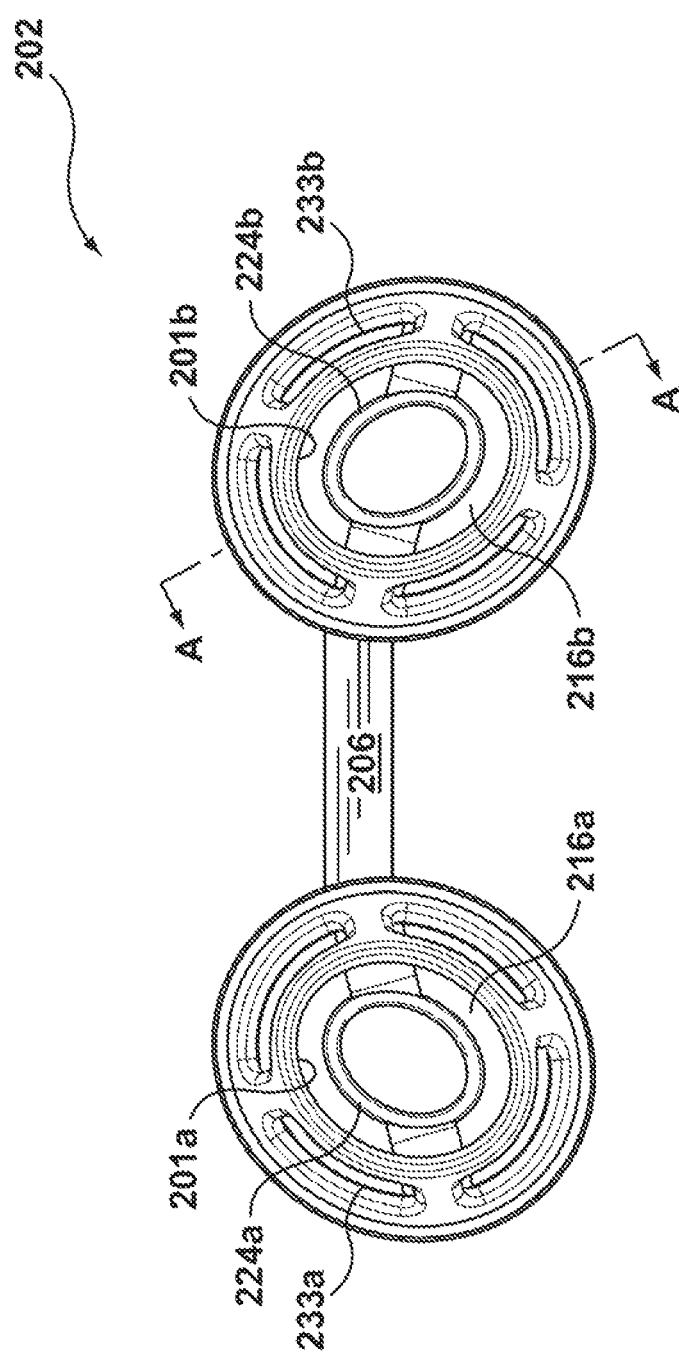
FIG. 13 is a top view of a portion of the nasal interface device of FIG. 11.
Figure 14:
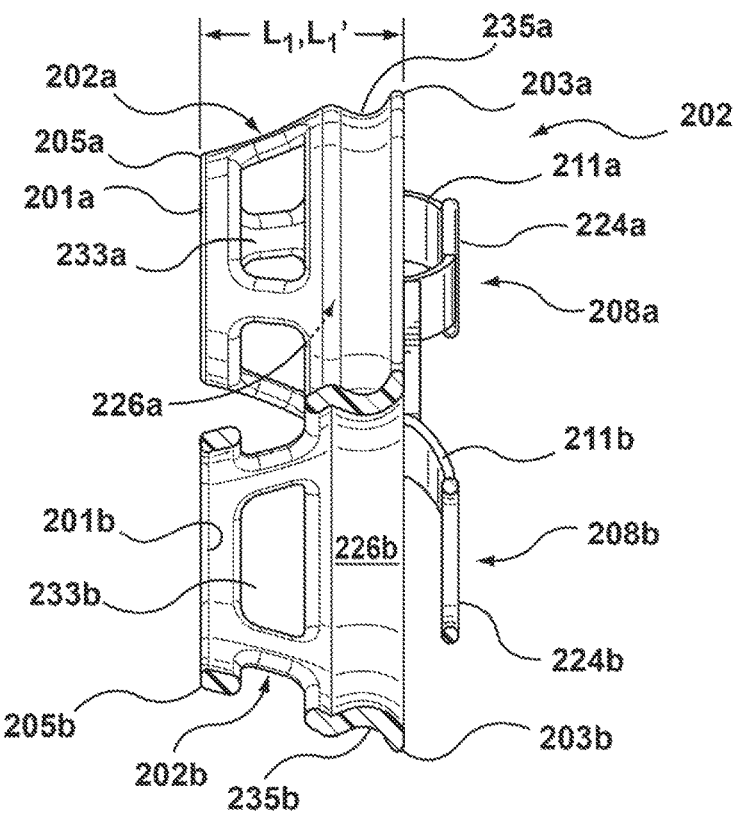
FIG. 14 is a partial sectional view of the portion of the nasal interface shown in FIG. 13 taken along line A-A thereof.
Figure 15:
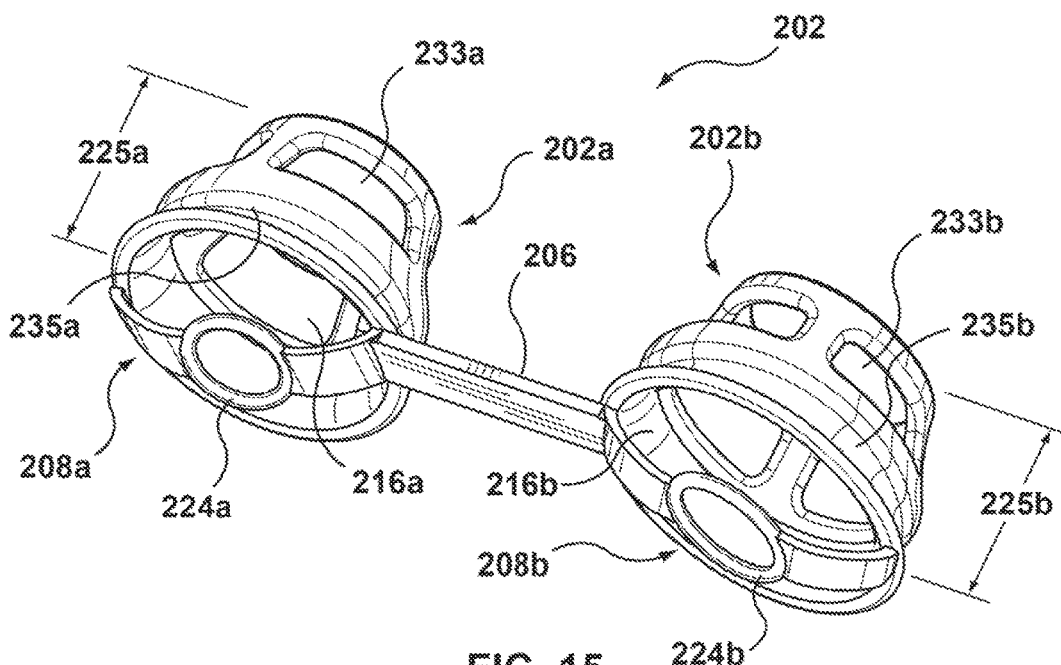
FIG. 15 is a perspective bottom view of the portion of the nasal interface shown in FIG. 13.

With reference to FIGS. 13 through 15, nasal pillow component 202 with nasal pillows 202a, 202b, connector strip 206 and distal support structures 208a, 208b is a unitary, contiguous molded component. In an embodiment, nasal pillow component 202 is of an elastomeric material, such as 30 Shore A silicone. Nasal pillows 202a, 202b are formed to have concave outer surfaces distal of first ends 203a, 203b that form grooves 235a, 235b for accommodating and/or contouring to a respective rim or lip of the nostril opening. As best shown in FIG. 15, distal support structures 208a, 208b include sealing rings 224a, 224b and struts or members 211a, 211b with each strut 211a, 211b laterally or radially extending between a respective sealing ring 224a, 224b and a respective first end 203a, 203b of a respective nasal pillow 202a, 202b. Although shown with two struts 211a, 211b, more or fewer struts may be used in support structures 208a, 208b in accordance with various embodiments hereof. Struts 211a, 211b are configured to permit a change in an aspect ratio of a cross-section of respective nasal pillows 202a, 202b from which they extend, which permits the respective nasal pillow to be squeezed radially inward or otherwise elastically deformed for insertion within a nostril and when released substantially return to their original shape to thereby anchor within a respective nostril to secure nasal interface 200 to the patient. In this manner, nasal interface 200 provides for a more comfortable and secure fit for the user. In an embodiment in which nasal pillow 202a, 202b have an oval cross-section the aspect ratio of the cross-section is the ratio of the larger diameter of the major axis of the ellipse to the smaller diameter of the minor axis of the ellipse. In an embodiment hereof, the flexibility of struts 211a, 211b permits the change in the aspect ratio of the cross-section of the respective nasal pillow 202a, 202b. In another embodiment, a shape of struts 211a, 211b permits the change in the aspect ratio of the cross-section of the respective nasal pillow 202a, 202b, such as the curved, thin and narrow strip-like or plank-like shape of struts 211a, 211b. In another embodiment, strut 211a, 211b may have a shape of a curved beam with a circular or square cross-section that permits the change in the aspect ratio of the cross-section of the respective nasal pillow 202a, 202b.

Hub components 204a, 204b include central hubs 210a, 210b having distal surfaces 221a, 221b through which a plurality of delivery openings 212a, 212b are formed and a proximal plenum structure 214a, 214b that defines an inlet 215a, 215b for receiving a compressed or pressurized respiratory gas and a plenum 217a, 217b for distributing the respiratory gas through the plurality of delivery openings 212a, 212b. Hub components 204a, 204b are attached to nasal pillow component 202 so as to be concentrically or axially disposed with respective distal ports 201a, 201b of nasal pillows 202a, 202b such that the plurality of delivery openings 212a, 212b of each central hub 210a, 210b are sized and positioned to deliver a respiratory gas within its respective nasal pillow. In an embodiment, distal surfaces 221a, 221b of central hubs 210a, 210b have a thickness or depth of less than 0.040 inch with each delivery opening 212a, 212b having a diameter of less than 0.010 inch.

In an embodiment, each of the plurality of delivery openings 212a, 212b forms a pattern in the distal surface of its respective central hub that corresponds to a shape of the corresponding distal port 201a, 201b. In an embodiment, hub components 204a, 204b are attached to nasal pillow component 202 by positioning a respective sealing ring 224a, 224b between its corresponding central hub 210a, 210b and proximal plenum structure 214a, 214b, and securing the respective central hub 210a, 210b and proximal plenum structure 214a, 214b together with the respective sealing ring 224a, 224b sandwiched therebetween. In embodiments hereof, each proximal plenum structure 214a, 214b is attached to its respective central hub 210a, 210b by any suitable means known to one of skill in the art, such as by a snap fit, gluing or welding.

In an embodiment hereof, outlet discs similar to outlet discs 122a, 122b may be used with central hubs 210a, 210b with the disc outlets being sized and configured to produce/deliver the pressurized respiratory gas/entrained air outflow stream to the respective nasal pillow proximal ports 201a, 201b. In such an embodiment, each of the plurality of delivery openings 212a, 212b would be adapted to have a diameter that is slightly greater than the diameter of a corresponding disc outlet such that each delivery opening 212a, 212b is large enough to not impede on the flow exiting from a corresponding disc outlet or outlets.

A series of ambient air apertures 216a, 216b are formed between respective portions of annular first ends 203a, 203b of nasal pillows 202a, 202b, adjacent struts 211a, 211b and central hubs 210a, 210b such that as shown in FIGS. 11, and 13-15, the series of ambient air apertures 216a, 216b of nasal interface 200 are disposed proximate to or near first ends 203a, 203b of each nasal pillow 202a, 202b, respectively, to substantially surround the respective hub components 204a, 204b disposed therein.

Nasal interface device 200 is fluidly connectable to a respiratory assist device via tubing for receiving the respiratory gas therefrom, as described above with reference to FIG. 8 that depicts nasal interface apparatus 130. Nasal interface device 200 also functions in a similar manner as described above with reference to the previous embodiment. More particularly with reference to FIG. 11A, which is a sectional view of a portion of nasal interface apparatus 200 within a patient's nostril, during an inspiratory phase of a patient wearing nasal interface device 200 as part of apparatus 130, the flow of a pressurized respiratory gas from the plurality of delivery openings 212b of central hub 210b in conjunction with entrained ambient air drawn from ambient air apertures 216b produces an outflow stream that substantially fills proximal port 201b prior to exiting nasal pillow 202b and entering a respective nare of the patient. During an expiratory phase of a patient wearing nasal interface device 200 as part of apparatus 130, the flow of the pressurized respiratory gas and thus entrainment of ambient air ceases and the patient is permitted to freely exhale through nasal interface 200 with the expired gas from the patient exiting through ambient air aperture 216b.

Figure 11A:
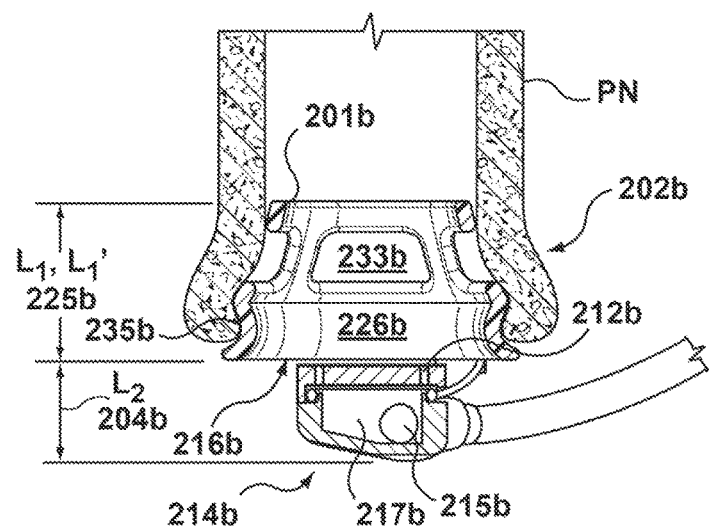
FIG. 11A is a sectional view of a portion of the nasal interface apparatus shown in FIG. 11 within a patient's nostril.

In an embodiment, an overall length $L_1'$ of each nasal pillow 202a, 202b is the same as a length $L_1$ of its tubular body portion 225a, 225b and is sized such that when nasal interface 200 is worn by a user the nasal pillow first end 203a, 203b does not extend beyond the nostril opening of the user with a rim or lip of the nostril opening fitting or abutting against a respective groove 235a, 235b of the nasal pillow 202a, 202b. With reference to FIG. 11A, length $L_1$, $L_1'$ of tubular body portion 225b/nasal pillow 202b is greater than a length $L_2$ of hub component 204b, with length $L_1$, $L_1'$ of tubular body portion 225b/nasal pillow 202b being sized to fit within the nostril of a user. In embodiments hereof, a length $L_1$ of tubular body portions 225a, 225b may be in the range of 0.10 inch to 0.60 inch and a length $L_2$ of hub components 204a, 204b may be in the range of 0.05 inch to 0.40 inch.

Figure 16:
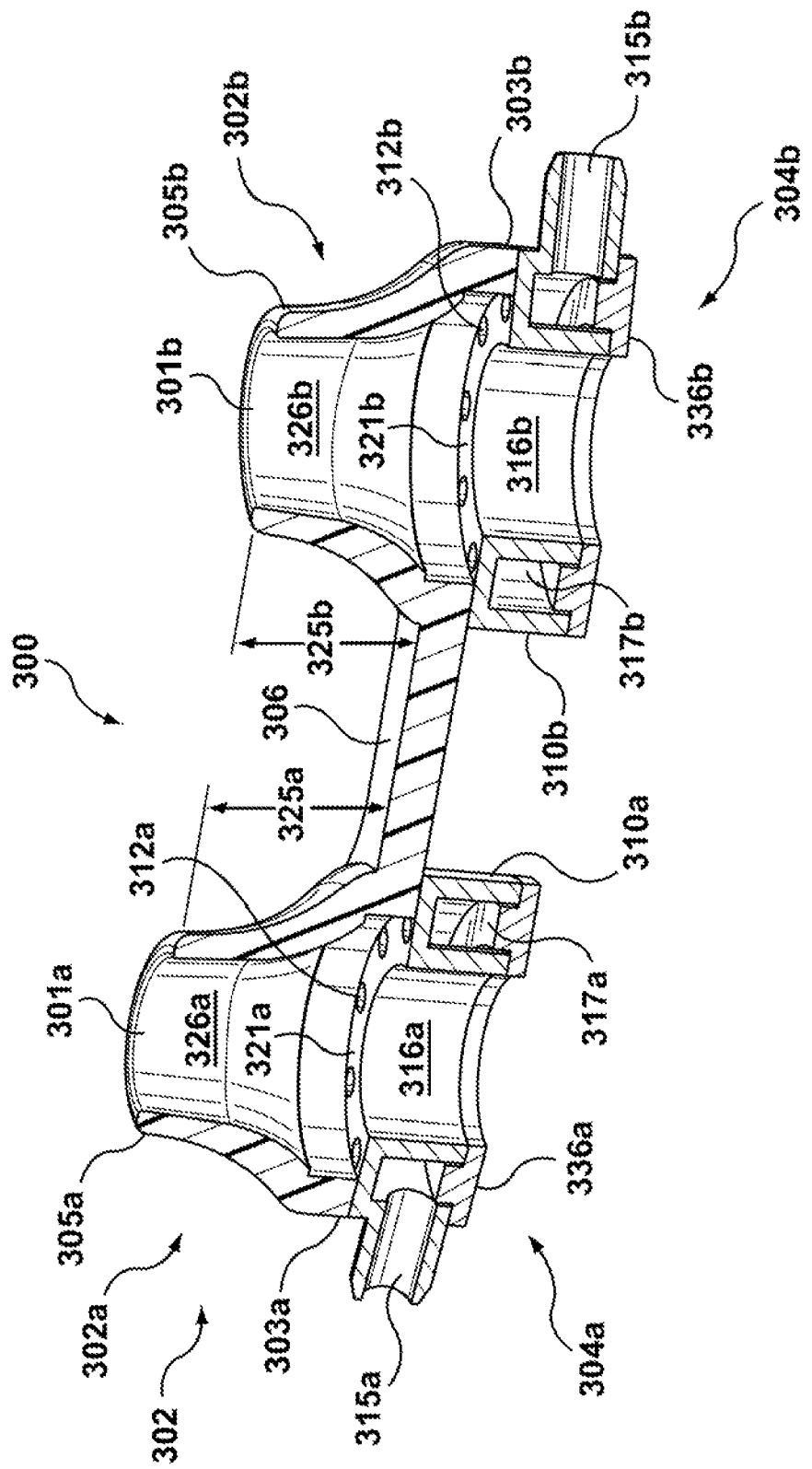
FIG. 16 is a sectional view of a nasal interface device in accordance with another embodiment hereof.

FIG. 16 is a sectional view of a nasal interface device 300 in accordance with another embodiment hereof, with FIGS. 17 and 18 being exploded perspective views showing various subcomponents of nasal interface device 300. The embodiment of FIGS. 16-18 may be used with all features described with reference to other embodiments hereof and only features and functions that differ from those already described will be detailed herein. Nasal interface 300 includes a nasal pillow component 302 and a pair of annular hub components 304a, 304b. "Annular" as used to describe various features of embodiments hereof means substantially shaped like a ring, hollow cylinder, or toroid and is not meant to be limited to a such shapes having a circular perimeter but is intended to include various other perimetrical shapes such as oval, elliptical, etc. Nasal pillow component 302 includes nasal pillows 302a, 302b with tubular body portions 325a, 325b defining central passageways 326a, 326b from substantially first or proximal ends 303a, 303b to respective second ends 305a, 305b thereof. Nasal pillow component 302 also includes a connector strip 306 that extends between nasal pillow first ends 303a, 303b to provide flexibility and articulation between nasal pillows 302a, 302b so as to permit adjustment to the particular anatomy of a user. In an embodiment, nasal pillow component 302 with nasal pillows 302a, 302b and connector strip 306 is a molded component of an elastomeric material, such as 30 Shore A silicone.

Annular hub components 304a, 304b are concentrically disposed with or at first ends 303a, 303b of nasal pillows 302a, 302b, respectively. With reference to the exploded views of nasal interface 300 depicted in FIGS. 17 and 18, each annular hub component 304a, 304b includes an annular hub 310a, 310b with a plurality of delivery openings 312a, 312b formed through distal surfaces 321a, 321b thereof, and a proximal annular cap 336a, 336b. The plurality of delivery openings 312a, 312b are periodically spaced about distal surfaces 321a, 321b so as to circumferentially surround centrally located ambient air apertures 316a, 316b. In conjunction with the positioning of the plurality of delivery openings 312a, 312b near to the ambient air apertures 316a, 316b, the plurality of delivery openings 312a, 312b are sized to produce/deliver the pressurized respiratory gas/entrained air outflow stream to the respective nasal pillow proximal ports 301a, 301b. In an embodiment, each of the plurality of delivery openings 312a, 312b has a circular cross-section. Annular hubs 310a, 310b define respective inlets 315a, 315b for receiving a respiratory gas from a respiratory assist device (not shown), and in conjunction with respective annular caps 336a, 336b form an enclosed space or plenum 317a, 317b for distributing the respiratory gas to the plurality of delivery openings 312a, 312b of the annular hub component. Annular caps 336a, 336b include distally extending annular flanges 318a, 318b that snap, or are otherwise secured by gluing or welding, within corresponding recesses within annular hubs 310a, 310b.

Annular hubs 310a, 310b of annular hub components 304a, 304b are positioned to be coaxial with respective distal ports 301a, 301b of nasal pillows 302a, 302b such that the plurality of delivery openings 312a, 312b of each annular hub component are positioned to deliver a respiratory gas within its respective nasal pillow. A central ambient air aperture 316a, 316b is formed by respective inner circumferential surfaces of annular hub components 304a, 304b so as to be disposed proximate to or near the plurality of delivery openings 312a, 312b of the respective annular hubs 310a, 310b at first ends 303a, 303b of nasal pillows 302a, 302b, respectively, as shown in FIG. 16.

In an embodiment hereof, outlet discs similar to outlet discs 122a, 122b may be used with central hubs 310a, 310b with the disc outlets being sized and configured to produce/deliver the pressurized respiratory gas/entrained air outflow stream to the respective nasal pillow proximal ports 301a, 301b. In such an embodiment, each of the plurality of delivery openings 312a, 312b would be adapted to have a diameter that is slightly greater than the diameter of a corresponding disc outlet such that each delivery opening 312a, 312b is large enough to not impede on the flow exiting from a corresponding disc outlet or outlets.

Nasal interface device 300 is fluidly connectable to a respiratory assist device via tubing for receiving the respiratory gas therefrom, as described above with reference to FIG. 8 that depicts nasal interface apparatus 130. Nasal interface device 300 also functions in a similar manner as described above with reference to nasal interface device 100. More particularly, during an inspiratory phase of a patient wearing nasal interface device 300 as part of apparatus 130, the flow of a pressurized respiratory gas from the plurality of delivery openings 312a, 312b of annular hubs 310a, 310b in conjunction with entrained ambient air drawn from centrally located ambient air apertures 316a, 316b produces an outflow stream that substantially fills proximal ports 301a, 301b prior to exiting nasal pillows 302a, 302b and entering a respective nare of the patient. During an expiratory phase of a patient wearing nasal interface device 300 as part of apparatus 130, the flow of the pressurized respiratory gas and thus entrainment of ambient air ceases and the patient is permitted to freely exhale through nasal interface 300 with the expired gas from the patient exiting through centrally located ambient air apertures 316a, 316b.

Figure 16A:
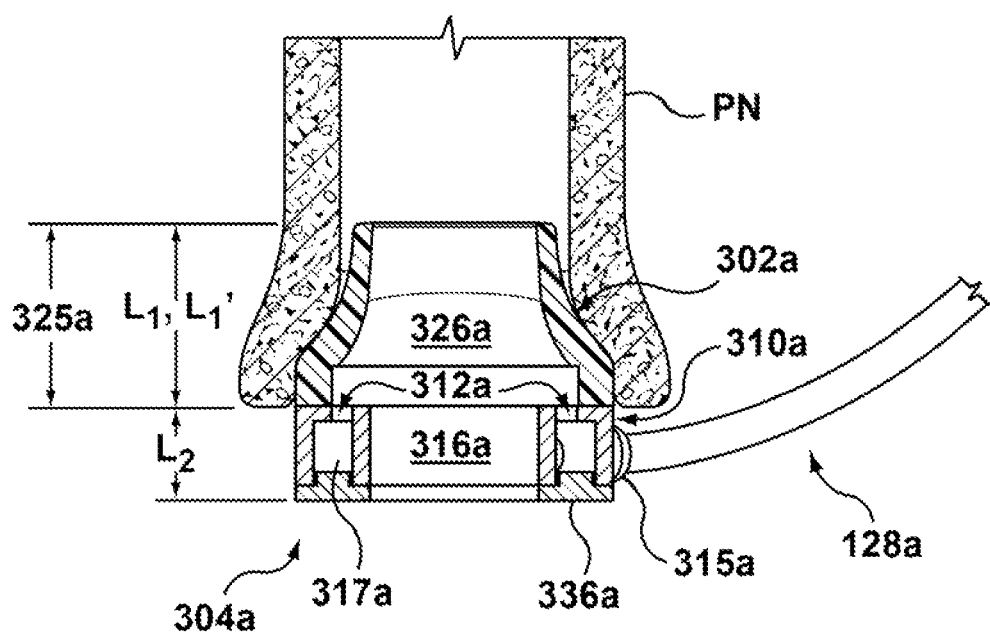
FIG. 16A is a sectional view of a portion of the nasal interface apparatus of FIG. 16 positioned within a patient's nostril.

FIG. 16A is a sectional view of a portion of nasal interface apparatus 300 of FIG. 16 positioned within a patient's nostril. An overall length L1' of each nasal pillow 302a, 302b is the same as a length L1 of its tubular body portion 325a, 325b and is sized such that when nasal interface 300 is worn by a user the nasal pillow first end 303a, 303b does not extend beyond the nostril of the user with a rim or lip of the nostril opening abutting against a respective first end 303a, 303b of the nasal pillow 302a, 302b. As depicted in FIG. 16A, length $L_1$, $L_1'$ of tubular body portion 325a/nasal pillow 302a is greater than a length $L_2$ of annular hub component 304a, with length $L_1$, $L_1'$ of tubular body portion 325a/nasal pillow 302a being sized to fit within the nostril of a user. In embodiments hereof, a length $L_1$ of tubular body portions 325a, 325b may be in the range of 0.10 inch to 0.60 inch and a length $L_2$ of hub components 304a, 304b may be in the range of 0.05 inch to 0.40 inch. In an embodiment, a length $L_1$ of tubular body portion 325a of nasal pillow 302a is sized to reside within the nostril of a user such that when nasal interface 300 is worn by the user connector strip 306 abuts against the columella C between the patient's nostrils while the remainder of the nasal interface 300, which includes annular hub component 304a, is disposed within or slightly proximal of the nostril of the user, as depicted in FIG. 16A. The use of the phrase "disposed . . . slightly proximal of the nostril of the user" is meant to convey that no part of the nasal pillow or hub component extends a distance proximal of the rim of the nostril opening that is sufficient to touch or interact with any tissue proximate or proximal of the rim of the nostril opening.

FIGS. 19 and 20 are schematic depictions of ambulatory assist ventilation (AAV) systems 1950, 2050 in accordance with embodiments hereof that may include any one of nasal interface devices 100, 200, 300, 400, 500, 600 as described above and a respiratory assist device 1952, 2052. In embodiments hereof, respiratory assist device 1952, 2052 are designed to be small and lightweight compared to existing respiratory ventilators which permits the device to be ambulatory. Respiratory assist device 1952, 2052 can either be worn by the user using a belt clip, shoulder strap or while residing in a pack such as a backpack or waist pack. Respiratory assist device 1952, 2052 can also be attached to the user's oxygen source (gaseous cylinder) eliminating the burden to the user of carrying the device. Common functionalities of AAV systems 1950, 2050 will be described together herein. AAV systems 1950, 2050 deliver mechanical ventilatory support or positive airway pressure to a patient, while permitting less encumbered movement so as to facilitate mobility of the patient and to allow activities of daily living. As a patient breathes in through one of nasal interface 100, 200, 300, 400, 500, 600, a negative pressure develops within the nasal pillows of the nasal interface that gets communicated through one or more sensing ports of the nasal interface to respiratory assist device 1952, 2052 and more particularly to a trigger or pressure sensor 1954, 2054 contained therein. With reference to the embodiment of FIG. 19, a continuous fluid flow passageway extends via tubing 1928 between trigger sensor 1954 and a central passageway of only one nasal pillow, with tubing 1928 having a first or proximal end coupled to respiratory assist device 1952 and a second or distal end couple to an inlet of the corresponding hub component of the nasal pillow. With reference to the embodiment of FIG. 20, a continuous fluid flow passageway extends via tubing 2028 between trigger sensor 2054 and central passageways of each of the pair of nasal pillows, with tubing 2028 having a first or proximal end coupled to respiratory assist device 2052 and a second or distal end coupled to a connector or fitting that couples to two tubes or length of tubing, such as tubing 128a, 128b shown in FIG. 8, that are attached to respective inlets of the hub components of the pair of nasal pillows.

Trigger sensor 1954, 2054 are configured to sense a negative pressure associated with an inspiratory phase of breathing, even a slight negative pressure, and when the negative pressure is sensed at a trigger value, logic controllers 1956, 2056 in response thereto open a control or solenoid valve 1958, 2058 to permit compressed respiratory gas to flow from compressed respiratory gas cylinders or reservoirs 1960, 2060 to pressure regulators 1964, 2064, which reduce the respiratory gas pressure, and then through respective flow orifice 1962, 2062 of the respiratory assist device to the nasal interface. In the embodiment of FIG. 19, the compressed respiratory gas flows to nasal interface 100, 200, 300 through tubing 1928, 1928', which in embodiments in accordance herewith may be or include lengths of tubing 128a, 128b as described above. In the embodiment of FIG. 20, the compressed respiratory gas flows to nasal interface 100, 200, 300 through tubing 2028 and 128a, 128b. The logic controllers 1956, 2056 are programmed to open control valves 1958, 2058 for a percentage of an inspiratory period and then to turn-off or close the control valve 1956, 2056/flow orifice 1962, 2062 until after exhalation. In this manner a patient or wearer of nasal interface 100, 200, 300 is able to freely exhale through the nasal interface, as described above.

In embodiments hereof, one or more of tubing 128a, 128b, 1928, 2028 defines a single lumen that is used both to provide fluid communication between the one or more sensing ports or openings of a corresponding hub component(s) of the nasal interface and the trigger sensor or pressure sensor of the respiratory assist device, and to deliver the compressed respiratory gas from the flow orifice of the respiratory assist device to the corresponding hub component(s) of the nasal interface. Single lumen tubing may be effectively used for combined sensing and respiratory gas delivery functionalities in embodiments hereof due to the efficient delivery of the compressed respiratory gas that is possible with nasal interfaces made in accordance with embodiments hereof. The efficient delivery of the compressed respiratory gas allows the use of regulated pressure respiratory gas, such as a compressed respiratory gas of less than 20 PSI, that does not adversely affect the trigger/pressure sensor during delivery of the lower pressure respiratory gas to the nasal pillows, such that the trigger/pressure sensor retains its functionality to sense very low pressures associated with triggering the next delivery of the respiratory gas. The use of a single lumen tube allows the reduction of the overall diameter of the tubing as compared to dual or multiple lumen tubing. This reduction in diameter allows further reduction in the interface size and the amount of 'bulk' that is strung across the users face. Additionally, a single lumen tube reduces the complexity of the circuit assembly by simplifying bifurcation points as well as connections to the interface and the respiratory assist devices as compared to multiple lumen tubing.

In various embodiments in accordance with the AAV system of FIG. 19, a sensing opening or openings of nasal interfaces 100, 200, 300, 400, 500, 600 may be one or more of the delivery openings of one of the hub components of the nasal interface. For example, sensing openings of a nasal interface 100 used with AAV device 1950 may be either the plurality of delivery openings 112a of hub component 104a, or alternatively may be the plurality of delivery openings 112b of hub component 104b depending upon which of the hub components 102a, 102b is connected via tubing 1928 to trigger/pressure sensor 1954 of respiratory assist device 1952.

In various embodiments in accordance with the AAV system of FIG. 20, a sensing opening or openings of nasal interfaces 100, 200, 300, 400, 500, 600 may be one or more of the delivery openings of each of the hub components of the nasal interface. For example, sensing openings of a nasal interface 100 used with AAV device 2050 may be the plurality of delivery openings 112a of hub component 104a and the plurality of delivery openings 112b of hub component 104b that are connected via tubing 128a, 128b and tubing 2028 to trigger/pressure sensor 2054 of respiratory assist device 2052.

Figure 21:
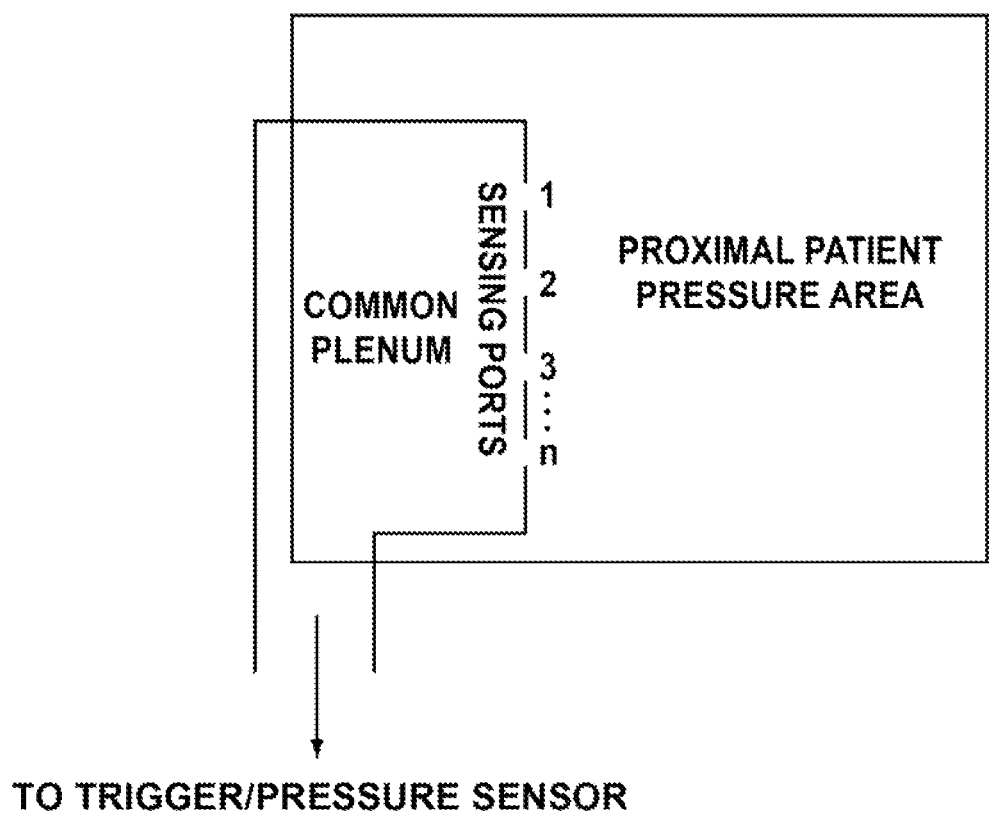
FIG. 21 is a schematic depiction of multiple pneumatically common sensing ports in accordance with embodiment hereof.

FIG. 21 is a schematic depiction of multiple pneumatically common sensing ports in accordance with embodiment hereof. AAV systems in accordance with embodiments hereof that contain multiple sensing ports or openings that have pneumatic commonality via a plenum, such as one or both plenums 117, 217, 317 of hub components 104, 204, 304 hereof, prior to communicating to a pressure sensing device, such as trigger/pressure sensors 1954, 2054, have at least two fundamental benefits. By spreading out locations of sensing ports/openings over an area, such as schematically represented by sense ports 1, 2, 3 . . . n in FIG. 21 and represented by delivery openings 112, 212, 312 in embodiments above, the pressure communicated to the trigger/pressure sensor of AAV systems 1952, 2052 will be roughly equivalent to the average of the pressure measured at each discrete sensing port across that area or $$P_{sensor} \approx (P_1 + P_2 + P_3 + \ldots + P_n) \div n,$$

with n being the total number of sensing ports.

With the sensing ports properly distributed over a surface of the plenum, such as when the sensing ports are the delivery openings as disclosed in accordance with embodiments hereof, a preferred average pressure across a sensing area may be established, which will reduce or eliminate the effect of localized velocity pressures that may occur at a single sensing port location. More particularly in known systems, velocity pressure at a single sensing port location, depending on flow direction, can disadvantageously either increase or reduce the static pressure measurement and thereby may yield erroneous pressure measurements that can ultimately affect the AAV system's ability to match the spontaneous breathing pattern of the user resulting in the system undesirably triggering out of synch. Such situations are avoided in accordance with embodiments hereof that include multiple sensing ports or openings that have pneumatic commonality via a plenum as described herein.

Additionally, with a size or diameter of each sensing port or opening being small relative to the plenum volume, multiple pneumatically common sensing ports in accordance with embodiments hereof will act as a low pass filter between the source pressure of the respiratory gas, a proximal patient pressure, and the trigger/pressure sensor. The low pass filter affect is created by and a function of the restriction of the orifices and the compliance of the plenum. If the restriction is increased, such as by reducing a size of the sensing opening, and/or the compliance of the plenum were to increase, such as by using a larger plenum, then the amount of filtering would increase. The low pass filtering affect is advantageous as it may improve the AAV systems synchrony with the patient by reducing false or missed triggers that may otherwise be caused by a higher frequency noise signal that occurs without the low pass filter affect.

Figure 22:
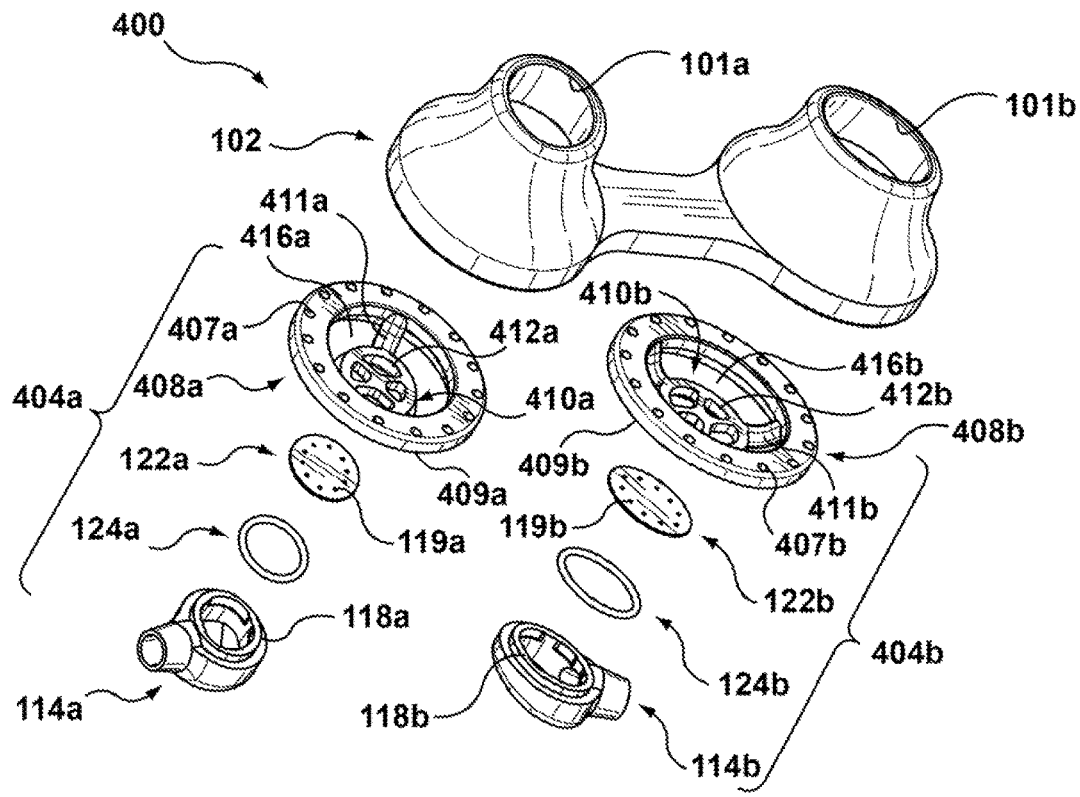
FIG. 22 is an exploded perspective view of a nasal interface device in accordance with another embodiment hereof showing various subcomponents thereof.
Figure 23:
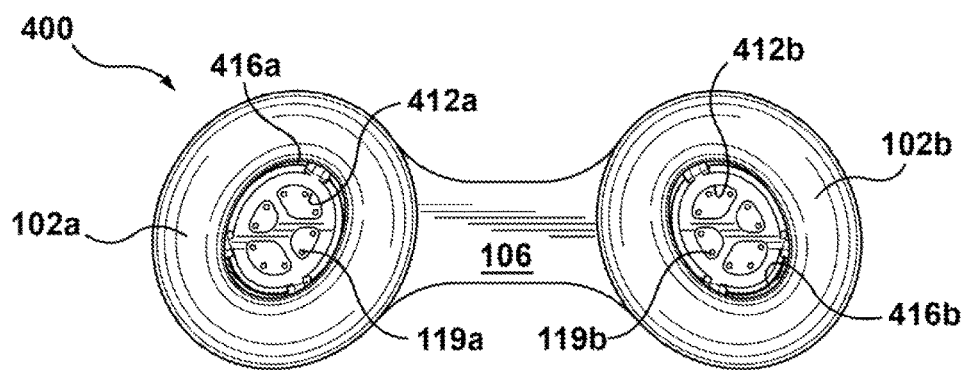
FIG. 23 is a top view of the nasal interface device of FIG. 22.

FIG. 22 is an exploded perspective view of a nasal interface device 400 in accordance with another embodiment hereof that shares features with nasal interface device 100 of FIGS. 1-7, with FIG. 23 depicting a top view of nasal interface device 400. The embodiment of FIGS. 22 and 23 may be used or adapted for use with all features described with reference to other embodiments hereof and only features and functions that differ from those already described will be detailed herein. Nasal interface 400 includes nasal pillow component 102 and a pair of hub components 404a, 404b. Each hub component 404a, 404b includes a distal support structure 408a, 408b, a central hub 410a, 410b with a plurality of delivery openings 412a, 412b, outlet discs 122a, 122b having a plurality of outlets 119a, 119b, seals 124a, 124b and proximal plenum structures 114a, 114b.

Hub components 404a, 404b, as described above, are attached to nasal pillow component 102 by respective annular rims 409a, 409b, each of which in the embodiment shown in FIGS. 22 and 23 includes a series of post-forming apertures 407a, 407b that receive a material of nasal pillow component 102 there through in an over-molding process that is used to connect the structures together. In another embodiment, nasal pillow component 102 may be glued or otherwise attached to annular rims 409a, 409b of hub components 404a, 404b. A series of ambient air apertures 416a, 416b are formed between respective annular rims 409a, 409b, adjacent spokes 411a, 411b and central hubs 410a, 410b.

The plurality of delivery openings 412a, 412b of each hub component 404a, 404b are spaced about a perimeter of distal face 421a, 421b of respective central hub 410a, 410b and are sized to be large enough to not impede on the flow exiting from two or more disc outlets 119a, 119b. Thus in the embodiment of FIGS. 22 and 23, the plurality of outlets 119a, 119b of outlet discs 122a, 122b do not directly correspond in number and arrangement to the plurality of delivery openings 412a, 412b of respective central hubs 410a, 410b. Outlet discs 122a, 122b and seals 124a, 124b are disposed within proximal recesses (not shown) of central hubs 410a, 410b such that the two or more disc outlets 119a, 119b substantially align with a corresponding central hub delivery opening 412a, 412b. In order to assure alignment of disc outlets 119a, 119b and delivery openings 412a, 412b, outlet discs 122a, 122b are held or pressed against respective proximal faces (not shown) of central hubs 410a, 410b by respective annular flanges 118a, 118b of proximal plenum structures 114a, 114b with seals 124a, 124b therebetween.

Figure 24:
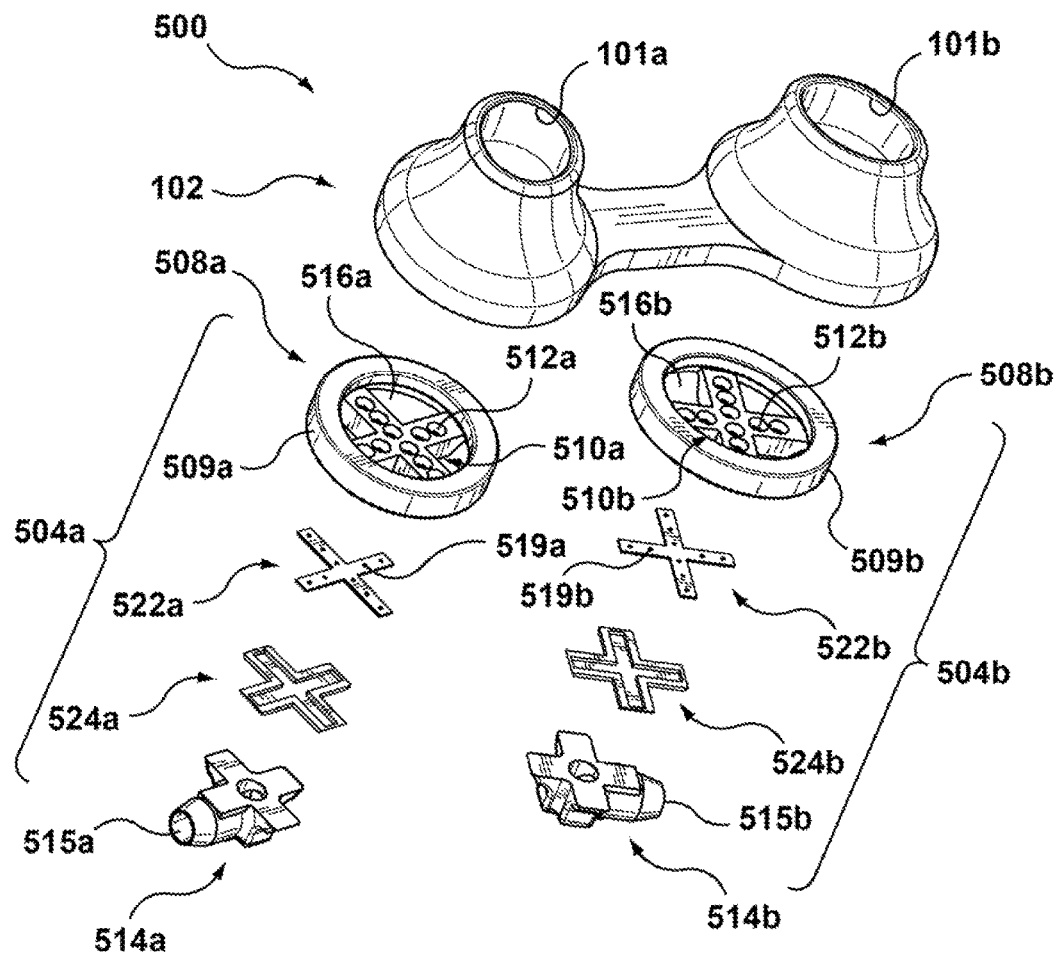
FIGS. 24 and 25 are exploded perspective views of a nasal interface device in accordance with another embodiment hereof showing various subcomponents thereof.
Figure 26:
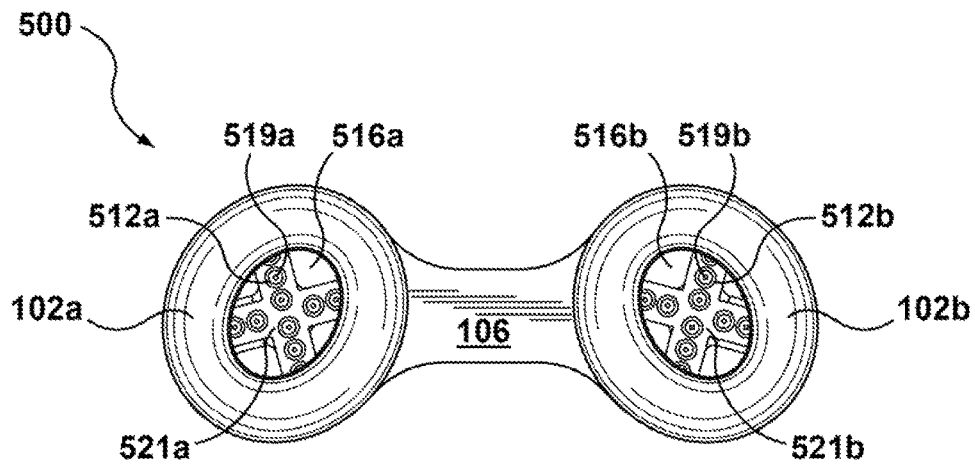
FIG. 26 is a top view of the nasal interface device of FIGS. 24 and 25.
Figure 25:
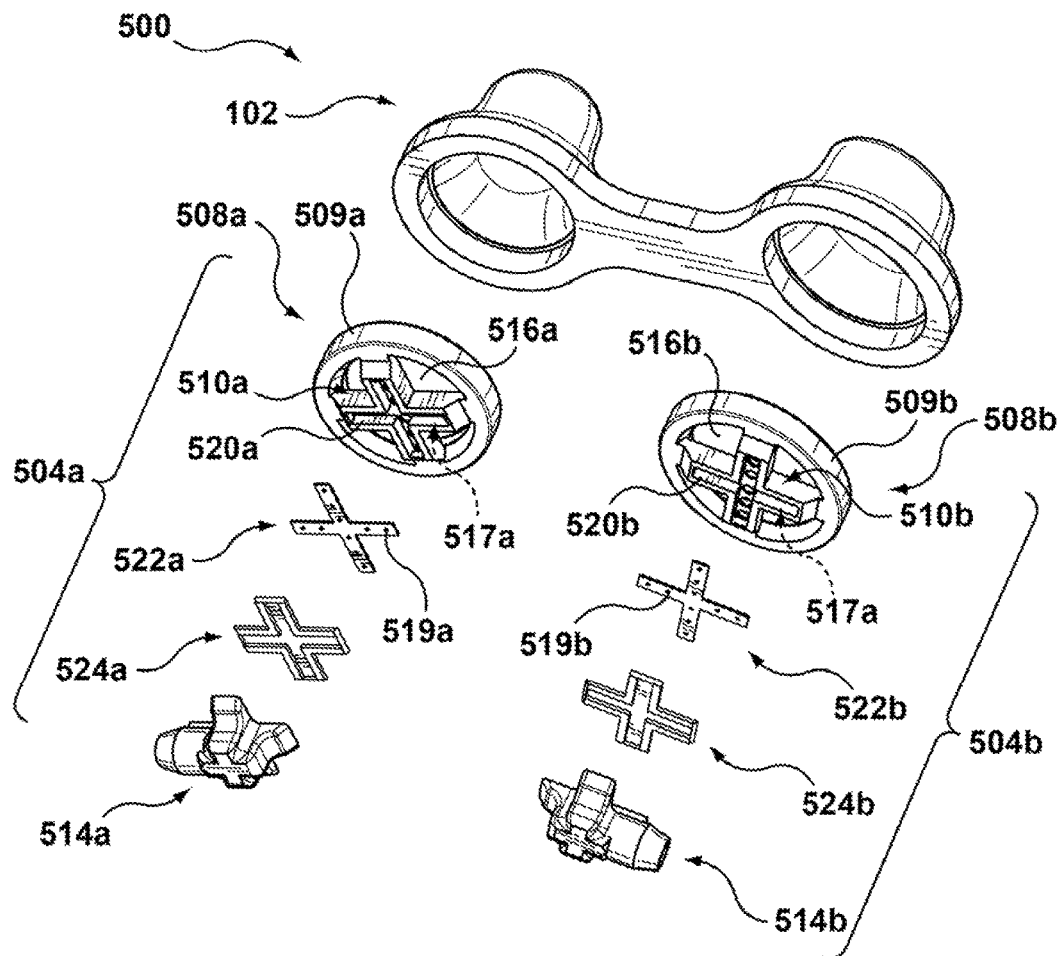
Figure 27:
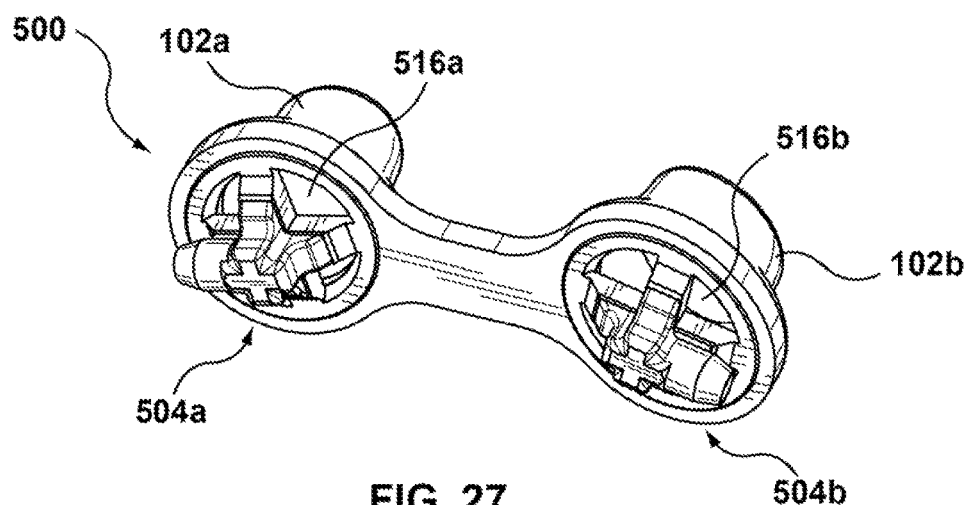
FIG. 27 is a perspective bottom view of the nasal interface device of FIGS. 24 and 25.

FIGS. 24 and 25 are exploded perspective views of a nasal interface device 500 in accordance with another embodiment hereof showing various subcomponents thereof, with FIG. 26 depicting a top view of nasal interface device 500 and FIG. 27 depicting a perspective bottom view of nasal interface device 500. The embodiment of FIGS. 24-27 may be used or adapted for use with all features described with reference to other embodiments hereof and only features and functions that differ from those already described will be detailed herein. Nasal interface 500 includes nasal pillow component 102 and a pair of hub components 504a, 504b. Each hub component 504a, 504b includes a distal support structure 508a, 508b, an X- or cross-shaped central hub 510a, 510b with a plurality of delivery openings 512a, 512b, X- or cross-shaped outlet discs 522a, 522b having a plurality of outlets 519a, 519b, X- or cross-shaped seals 524a, 524b and X- or cross-shaped proximal plenum structures 514a, 514b.

Respective annular rims 509a, 509b of hub components 504a, 504b, as described above, are attached to nasal pillow component 502 by gluing, welding or the like, and in another embodiment may include a series of post-forming apertures for receiving a material of nasal pillow component 102 there through in an over-molding process. A series of ambient air apertures 516a, 516b are formed between respective annular rims 509a, 509b, and X- or cross-shaped central hubs 510a, 510b.

Central hubs 510a, 510b of hub components 504a, 504b are positioned to longitudinally align with respective distal ports 101a, 101b of nasal pillows 102a, 102b such that the plurality of disc outlets 519a, 519b and delivery openings 512a, 512b of each hub are positioned to deliver a respiratory gas within its respective nasal pillow. Proximal plenum structures 514a, 514b of hub components 504a, 504b define an inlet 515a, 515b for receiving a respiratory gas from the respiratory assist device (not shown) and a plenum or chamber 517a, 517b for distributing the respiratory gas to the plurality of disc outlets 519a, 519b and delivery openings 512a, 512b of respective central hubs 510a, 510b. More particularly, a respective plenum 517a, 517b is formed when a proximal plenum structure 514a, 514b is secured or otherwise attached to a corresponding central hub 510a, 510b to be defined by proximal recesses 520a, 520b therebetween. Proximal plenum structures 514a, 514b are shaped and sized to snap or fit within corresponding proximal recesses 520a, 520b within central hubs 510a, 510b, to be secured therein by ultrasonic welding, gluing or the like.

The plurality of delivery openings 512a, 512b of each hub component 504a, 504b are periodically spaced along X- or cross-shaped distal face 521a, 521b of respective central hub 510a, 510b and are sized to be large enough to not impede on the flow exiting from a corresponding disc outlet 519a, 519b, as best shown in FIG. 26. Thus in the embodiment of FIGS. 24-27, the plurality of outlets 519a, 519b of outlet discs 522a, 522b directly correspond in number and arrangement to the plurality of delivery openings 512a, 512b of respective central hubs 510a, 510b. Outlet discs 522a, 522b and seals 524a, 524b are disposed within proximal recesses 520a, 520b of central hubs 510a, 510b such that the disc outlets 519a, 519b substantially align with corresponding central hub delivery openings 512a, 512b. In order to assure alignment of disc outlets 519a, 519b and delivery openings 512a, 512b, outlet discs 522a, 522b are held or pressed against respective proximal faces (not shown) of central hubs 510a, 510b by proximal plenum structures 514a, 514b being received within proximal recesses 520a, 520b to press seals 224a, 224b against an edge or perimeter of respective outlet discs 522a, 522b.

Figure 28:
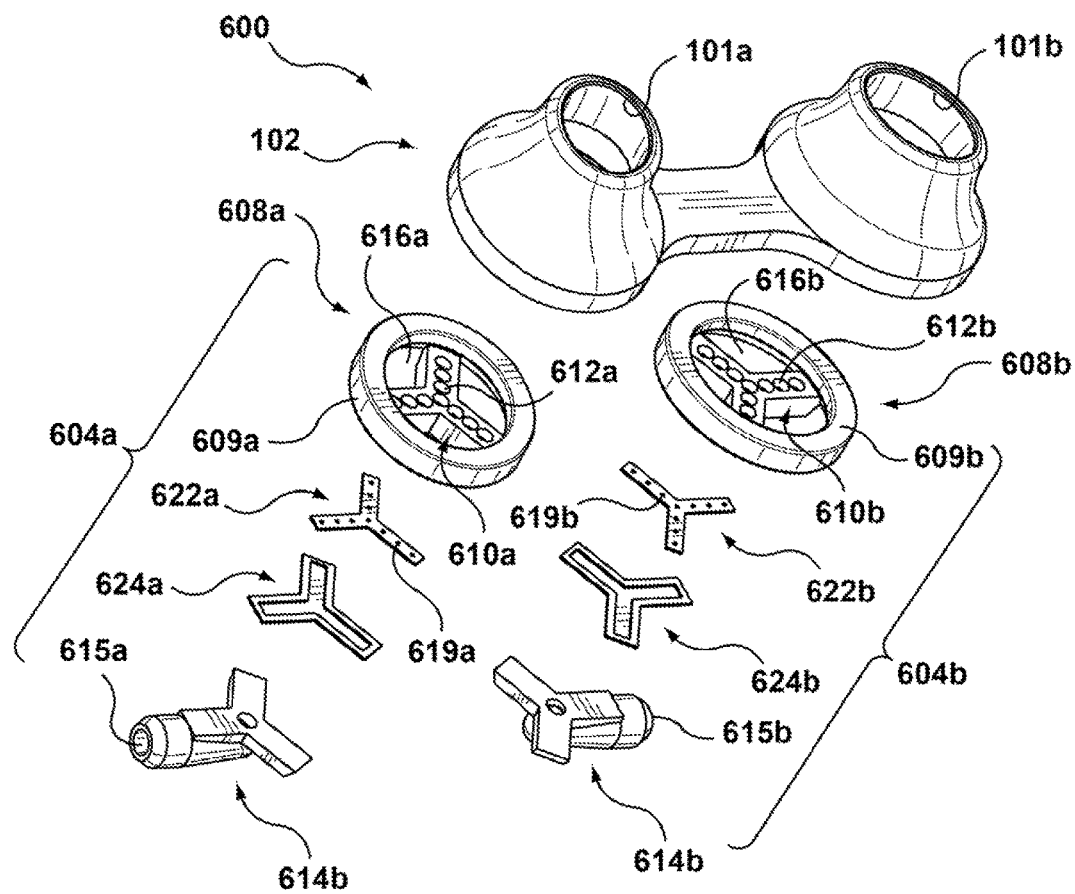
FIGS. 28 and 29 are exploded perspective views of a nasal interface device in accordance with another embodiment hereof showing various subcomponents thereof.
Figure 30:
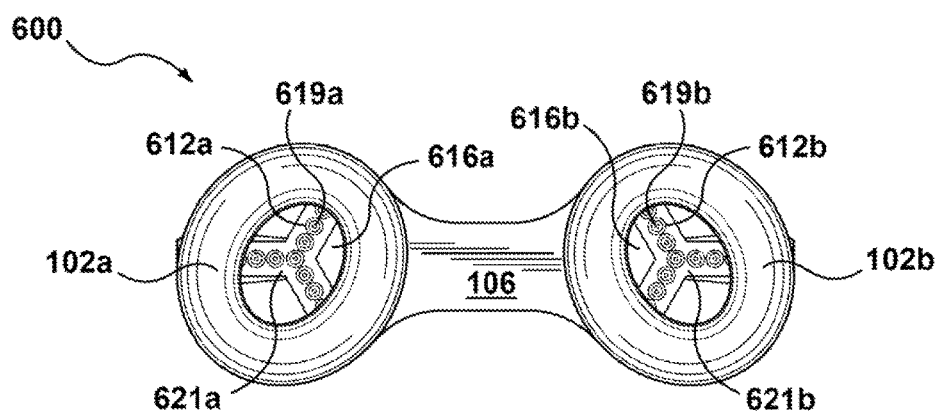
FIG. 30 is a top view of the nasal interface device of FIGS. 28 and 29.
Figure 29:
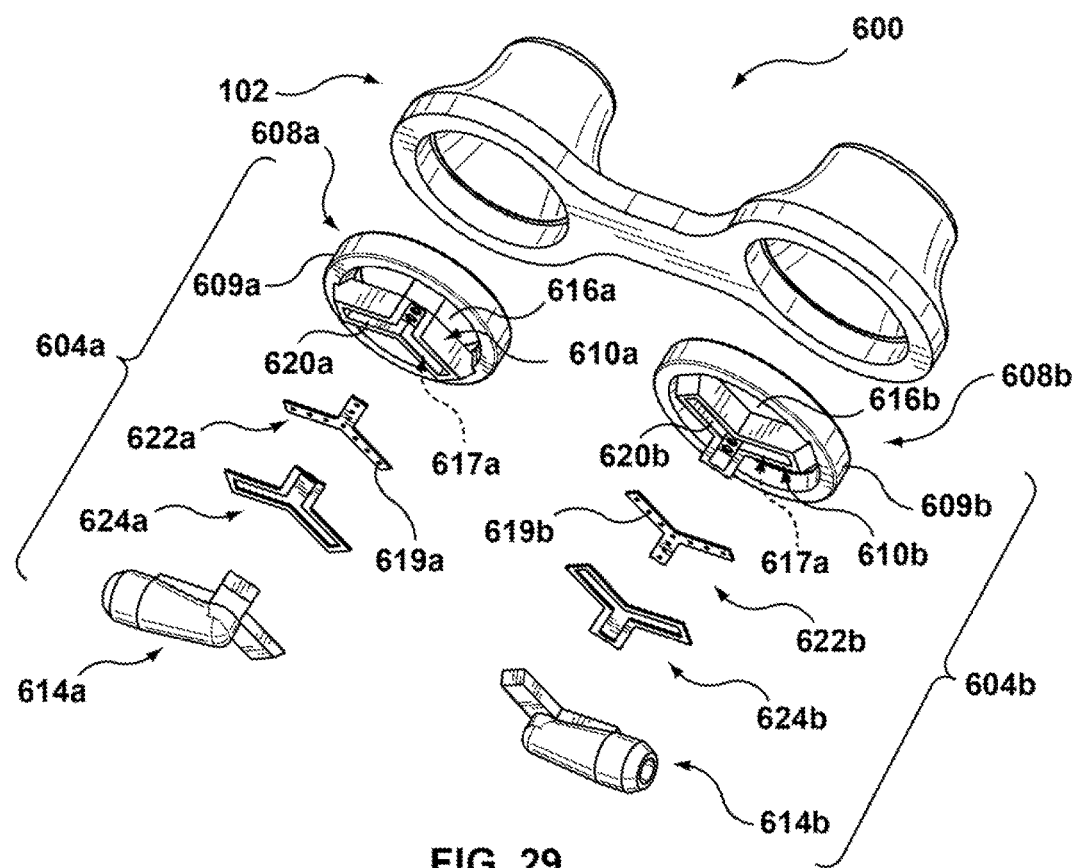
Figure 31:
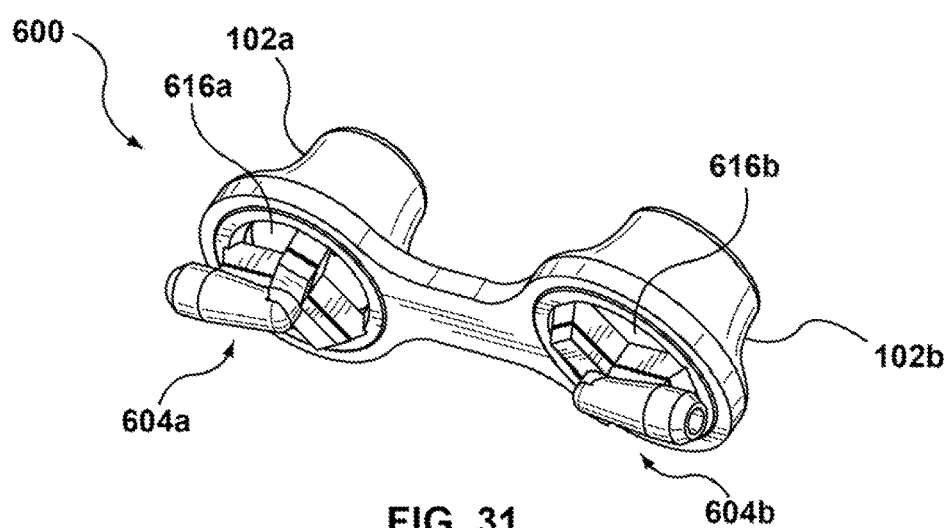
FIG. 31 is a perspective bottom view of the nasal interface device of FIGS. 28 and 29.

FIGS. 28 and 29 are exploded perspective views of a nasal interface device 600 in accordance with another embodiment hereof showing various subcomponents thereof, with FIG. 30 depicting a top view of nasal interface device 600 and FIG. 31 depicting a perspective bottom view of nasal interface device 600. The embodiment of FIGS. 28-31 may be used or adapted for use with all features described with reference to other embodiments hereof and only features and functions that differ from those already described will be detailed herein. Nasal interface 600 includes nasal pillow component 102 and a pair of hub components 604a, 604b. Each hub component 604a, 604b includes a distal support structure 608a, 608b, an Y-shaped central hub 610a, 610b with a plurality of delivery openings 612a, 612b, Y-shaped outlet discs 622a, 622b having a plurality of outlets 619a, 619b, Y-shaped seals 624a, 624b and Y-shaped proximal plenum structures 614a, 614b.

Respective annular rims 609a, 609b of hub components 604a, 604b, as described above, are attached to nasal pillow component 602 by gluing, welding or the like, and in another embodiment may include a series of post-forming apertures for receiving a material of nasal pillow component 102 there through in an over-molding process. A series of ambient air apertures 616a, 616b are formed between respective annular rims 609a, 609b, and Y-shaped central hubs 610a, 610b.

Central hubs 610a, 610b of hub components 604a, 604b are positioned to longitudinally align with respective distal ports 101a, 101b of nasal pillows 102a, 102b such that the plurality of disc outlets 619a, 619b and delivery openings 612a, 612b of each hub are positioned to deliver a respiratory gas within its respective nasal pillow. Proximal plenum structures 614a, 614b of hub components 604a, 604b define an inlet 615a, 615b for receiving a respiratory gas from the respiratory assist device (not shown) and a plenum or chamber 617a, 617b for distributing the respiratory gas to the plurality of disc outlets 619a, 619b and delivery openings 612a, 612b of respective central hubs 610a, 610b. More particularly, a respective plenum 617a, 617b is formed when a proximal plenum structure 614a, 614b is secured or otherwise attached to a corresponding central hub 610a, 610b to be defined by proximal recesses 620a, 620b therebetween. Proximal plenum structures 614a, 614b are shaped and sized to snap or fit within corresponding proximal recesses 620a, 620b within central hubs 610a, 610b, to be secured therein by ultrasonic welding, gluing or the like.

The plurality of delivery openings 612a, 612b of each hub component 604a, 604b are periodically spaced along Y-shaped distal face 621a, 621b of respective central hub 610a, 610b and are sized to be large enough to not impede on the flow exiting from a corresponding disc outlet 619a, 619b, as best shown in FIG. 30. Thus in the embodiment of FIGS. 28-31, the plurality of outlets 619a, 619b of outlet discs 622a, 622b directly correspond in number and arrangement to the plurality of delivery openings 612a, 612b of respective central hubs 610a, 610b. Outlet discs 622a, 622b and seals 624a, 624b are disposed within proximal recesses 620a, 620b of central hubs 610a, 610b such that the disc outlets 619a, 619b substantially align with corresponding central hub delivery openings 612a, 612b. In order to assure alignment of disc outlets 619a, 619b and delivery openings 612a, 612b, outlet discs 622a, 622b are held or pressed against respective proximal faces (not shown) of central hubs 610a, 610b by proximal plenum structures 614a, 614b being received within proximal recesses 620a, 620b to press seals 624a, 624b against an edge or perimeter of respective outlet discs 622a, 622b.

While various embodiments have been described above, it should be understood that they have been presented only as illustrations and examples of the present invention, and not by way of limitation. It will be apparent to persons skilled in the relevant art that various changes in form, shape, arrangement and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A nasal interface apparatus for use with a respiratory device that doses compressed gas from a compressed gas source, the apparatus comprising:
    a pair of hub assemblies for receiving the compressed gas, each hub assembly having a plurality of air apertures through which ambient air is permitted to flow and a plurality of openings configured to deliver the compressed gas within an outlet flow area defined along a perimeter that runs proximate to the plurality of air apertures such that substantially all of the compressed gas is delivered along the perimeter; and
    a pair of nasal pillows, wherein each nasal pillow has a tubular structure with a first end and a second end, and wherein a respective hub assembly is positioned within the first end of each nasal pillow.

2. The nasal interface apparatus of claim 1 further comprising:
    a connector strip that extends between the pair of nasal pillows.

3. The nasal interface apparatus of claim 2, wherein the nasal pillows, the connector strip and support structures for attaching the nasal pillows to the hub assemblies are an integral unitary part.

4. The nasal interface apparatus of claim 3, wherein the nasal pillows have concave outer surfaces proximate the first ends thereof that form grooves for accommodating a respective nostril rim of a user.

5. The nasal interface apparatus of claim 3, wherein each of the support structures includes a sealing ring and a strut with the strut extending between the sealing ring and the first end of the respective nasal pillow.

6. The nasal interface apparatus of claim 5, wherein the strut is configured to permit a change in an aspect ratio of a cross-section of the nasal pillow for insertion within a nostril.

7. The nasal interface apparatus of claim 6, wherein the flexibility of the strut permits the change in the aspect ratio of the cross-section of the nasal pillow.

8. The nasal interface apparatus of claim 6, wherein a shape of the strut permits the change in the aspect ratio of the cross-section of the nasal pillow.

9. The nasal interface apparatus of claim 5, wherein the hub assemblies are attached to the sealing rings so as to be concentrically disposed within their respective nasal pillows.

10. The nasal interface apparatus of claim 9, wherein each hub assembly includes a central hub through which the plurality of openings are formed and a proximal component that defines an inlet for receiving the compressed gas and a plenum for distributing the compressed gas through the plurality of openings.

11. The nasal interface apparatus of claim 10, wherein the respective sealing ring is positioned between the central hub and the proximal component when the respective hub assembly is attached thereto.

12. The nasal interface apparatus of claim 2, wherein a length of the body portion of the nasal pillow is sized to fit within a nostril of a user such that, when the nasal interface is worn by the user, the connector strip abuts against the columella of the user while a remainder of the nasal interface is disposed within or slightly proximal of the nostril of the user.

13. The nasal interface apparatus of claim 1, wherein a length of each nasal pillow is greater than a length of its respective hub assembly.

14. The nasal interface apparatus of claim 1, wherein the tubular structures of the nasal pillows have lattice-like walls.

15. The nasal interface apparatus of claim 1, wherein each of the hub assemblies includes an inlet for receiving the compressed gas and a plenum for distributing the compressed gas through the plurality of openings.

16. The nasal interface apparatus of claim 15, wherein the plurality of openings of each hub assembly are in fluid communication with a corresponding plurality of outlets formed through an outlet disc that is secured to the hub assembly to be in fluid communication with the plenum.

17. The nasal interface apparatus of claim 16, wherein each of the plurality of outlets of the outlet disc has a diameter of less than 0.010 inches and a depth of less than 0.040 inches.

18. The nasal interface of claim 17, wherein each of the plurality of openings is sized to be large enough to not impede the flow of compressed gas exiting from a corresponding disc outlet.

19. The nasal interface apparatus of claim 15, wherein tubing is coupled to each of the hub assembly inlets to provide fluid communication between the nasal interface and the respiratory device.

20. The nasal interface apparatus of claim 19, wherein the tubing has a first inner diameter where the tubing connects with the respective hub assembly inlet and a second inner diameter that is greater than the first inner diameter where the tubing connects with the respiratory device.

21. The nasal interface apparatus of claim 20, wherein the tubing is formed from segments of tubing that are connected together with at least a first segment having the first inner diameter connected to the respective hub assembly inlets and a second segment having the second inner diameter connected to the respiratory device.

22. The nasal interface of claim 1, wherein the plurality of air apertures is a series of ambient air apertures that substantially surround the plurality of openings of the respective hub assembly.

23. The nasal interface apparatus of claim 1, wherein a distal surface of a central hub of each hub assembly includes the plurality of openings formed therein.

24. The nasal interface apparatus of claim 23, wherein the distal surface of each central hub is aligned with a proximal surface of a respective nasal pillow.

25. The nasal interface apparatus of claim 24, wherein the nasal pillows are attached to support structures of the hub assemblies.

26. The nasal interface apparatus of claim 25, wherein each of the support structures includes an outer annular rim attached to the first end of the respective nasal pillow and at least one spoke extending between the outer annular rim and a central hub of the hub assembly that includes the plurality of openings formed therein such that the central hub is coaxially disposed within the nasal pillow by the at least one spoke.

27. The nasal interface apparatus of claim 26, wherein the plurality of air apertures are openings defined between the outer annular rim, the central hub, and the at least one spoke.

28. The nasal interface apparatus of claim 23, wherein the distal surface of each central hub is disposed proximal to a proximal surface of the respective nasal pillow.

29. The nasal interface apparatus of claim 23, wherein the distal surface of each central hub is disposed distal to a proximal surface of the respective nasal pillow.

30. The nasal interface apparatus of claim 23, wherein each of the plurality of openings of the central hubs has a diameter of less than 0.010 inches and a length of approximately 0.040 inches.

31. The nasal interface apparatus of claim 1, wherein at least one hub assembly includes at least one opening for sensing.

32. The nasal interface apparatus of claim 31, wherein the at least one opening for sensing is one of the plurality of openings of the hub assembly.

33. The nasal interface apparatus of claim 1, wherein a length of the body portion of the nasal pillow is sized to fit within a nostril of a user such that, when the nasal interface is worn by the user, the first end of the nasal pillow does not substantially extend beyond the nostril of the user.

34. The nasal interface of claim 1, wherein each hub assembly further comprises a central hub having the plurality of openings formed therethrough and a proximal plenum structure attached to the central hub that defines a plenum for distributing the compressed gas through the plurality of openings.

35. The nasal interface of claim 34, wherein the central hub and proximal plenum structure are one of an oval shape, a cross- or X-shape, and a Y-shape.

36. The nasal interface apparatus of claim 35, wherein the plurality of openings of each hub assembly are in fluid communication with a corresponding plurality of outlets formed through an outlet disc that is secured to the hub assembly to be in fluid communication with the plenum, wherein the outlet disc is of a shape that corresponds to the shape of the central hub and proximal plenum structure.

37. The nasal interface apparatus of claim 36, wherein each of the plurality of outlets of the outlet disc has a diameter of less than 0.010 inches and a depth of less than 0.040 inches.

38. The nasal interface apparatus of claim 34, wherein the plurality of openings of each central hub are arranged in one of an oval, a circular, a polygonal, a cross, and a series of parallel lines pattern.

39. A nasal interface apparatus for use with a respiratory device that doses compressed gas from a compressed gas source, the apparatus comprising:

first and second hub assemblies for receiving the compressed gas, wherein each of the first and second hub assemblies defines a plenum for distributing the compressed gas, each of the first and second hub assemblies having a plurality of air apertures through which ambient air is permitted to flow and a plurality of openings configured to deliver the compressed gas within an outlet flow area defined along a perimeter that runs proximate to the plurality of air apertures such that substantially all of the compressed gas is delivered proximate to the plurality of air apertures, and wherein the first hub assembly includes a sensing opening in fluid communication with a pressure sensor of the respiratory device;

a first nasal pillow having the first hub assembly positioned within a proximal end thereof;

a second nasal pillow having the second hub assembly positioned within a proximal end thereof; and a first tube coupled to an inlet of the first hub plenum, wherein the first tube has a single lumen for delivering the compressed gas to the first hub assembly and for providing fluid communication between the sensing opening of the first hub assembly and the pressure sensor.

40. The nasal interface apparatus of claim 39, wherein one of the plurality of openings of the first hub assembly is also the sensing opening of the first hub assembly.

41. The nasal interface apparatus of claim 39, further comprising:

a second tube coupled to an inlet of the second hub plenum for delivering the compressed gas to the second hub assembly.

42. The nasal interface apparatus of claim 41, wherein the first and second tubes have flared or stepped-up diameter segments that are disposed along lengths of the respective tubes that lie proximal of a user's ears when the nasal interface apparatus is in use.

43. The nasal interface apparatus of claim 42, wherein the first and second tubes have a first inner diameter from first ends of the first and second tubes to the flared or stepped-up diameter segments and a second inner diameter that is greater than the first inner diameter from the flared or stepped-up diameter segments to second ends of the first and second tubes.

44. The nasal interface apparatus of claim 39, wherein the plurality of openings of each of the first and second hub assemblies are spaced about a perimeter of a respective central hub of the respective hub assembly.

45. The nasal interface apparatus of claim 44, further comprising:

at least one air aperture disposed between the proximal end of the first nasal pillow and the central hub of the first hub assembly; and at least one air aperture disposed between the proximal end of the second nasal pillow and the central hub of the second hub assembly.

46. The nasal interface apparatus of claim 39, further comprising:
a connector strip that connects together the proximal ends of the first and second nasal pillows.

47. A nasal interface apparatus for use with a respiratory device that doses compressed gas from a compressed gas source, the apparatus comprising:
a pair of annular hub assemblies for receiving the compressed gas, each hub assembly having a plurality of air apertures through which ambient air is permitted to flow and a plurality of openings configured to deliver the compressed gas within an outlet flow area defined along a perimeter that runs proximate to the plurality of air apertures such that substantially all of the compressed gas is delivered along the perimeter; and
a pair of nasal pillows, wherein each nasal pillow has a respective annular hub assembly positioned within a proximal end thereof.

48. The nasal interface apparatus of claim 47, wherein an inner circumferential surface of each annular hub assembly defines the plurality of air apertures through the respective annular hub assembly.

49. The nasal interface apparatus of claim 48, wherein the plurality of air apertures is concentrically disposed within the proximal end of the nasal pillow.

50. The nasal interface apparatus of claim 47 further comprising:
a connector strip that connects together the proximal ends of the pair of nasal pillows.

51. The nasal interface apparatus of claim 47, wherein a length of the annular hub assemblies is less than a length of the nasal pillows.

52. The nasal interface apparatus of claim 47, wherein each of the annular hub assemblies defines an inlet for receiving the compressed gas and a plenum for distributing the compressed gas through the plurality of openings.

53. The nasal interface apparatus of claim 47, wherein at least one annular hub assembly includes at least one opening for sensing.

54. The nasal interface apparatus of claim 53, wherein the at least one opening for sensing is one of the plurality of openings of the annular hub assembly.

* * * * *